United States Patent
Guevremont et al.

(10) Patent No.: US 7,223,971 B2
(45) Date of Patent: May 29, 2007

(54) METHOD AND APPARATUS FOR SELECTING INLETS OF A MULTIPLE INLET FAIMS

(75) Inventors: Roger Guevremont, Ottawa (CA); Govindanunny Thekkadath, Ottawa (CA); Greg Skotnicki, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 38 days.

(21) Appl. No.: 11/068,767

(22) Filed: Mar. 2, 2005

(65) Prior Publication Data
US 2005/0194532 A1  Sep. 8, 2005

Related U.S. Application Data

(60) Provisional application No. 60/549,170, filed on Mar. 3, 2004.

(51) Int. Cl.
*B01D 59/44* (2006.01)
(52) U.S. Cl. .......................... 250/294; 250/288; 250/292
(58) Field of Classification Search ................ 250/292, 250/294
See application file for complete search history.

(56) References Cited

U.S. PATENT DOCUMENTS

| | | | |
|---|---|---|---|
| 5,420,424 A | 5/1995 | Carnahan et al. | |
| 6,495,823 B1 | 12/2002 | Miller et al. | |
| 6,504,149 B2 | 1/2003 | Guevremont et al. | |
| 6,621,077 B1 | 9/2003 | Guevremont et al. | |
| 6,653,627 B2 | 11/2003 | Guevremont et al. | |
| 6,690,004 B2 | 2/2004 | Miller et al. | |
| 6,753,522 B2 | 6/2004 | Guevremont et al. | |
| 6,784,422 B2 | 8/2004 | Covey et al. | |
| 6,787,765 B2 | 9/2004 | Guevremont et al. | |
| 7,041,969 B2* | 5/2006 | Guevremont et al. | 250/285 |
| 2004/0232326 A1 | 11/2004 | Guevremont et al. | |
| 2005/0194527 A1* | 9/2005 | Guevremont et al. | 250/285 |

FOREIGN PATENT DOCUMENTS

WO  WO 03/067625 A1  8/2003

* cited by examiner

*Primary Examiner*—David Vanore
(74) *Attorney, Agent, or Firm*—Freedman & Associates

(57) ABSTRACT

An ion introduction system for selecting ions from one of two separate ionization sources of ions is provided. The system includes a plate having a hole formed therethrough, the plate for being disposed adjacent an ion introduction region of a gas phase ion analyzer such that the hole is selectively movable between a first location in which the hole is adjacent to a first ionization source of ions for supporting introduction of ions from the first ionization source of ions into the gas phase ion analyzer, and a second location in which the hole is adjacent to a second ionization source of ions for supporting introduction of ions from the second ionization source of ions into the gas phase ion analyzer. The system also includes a drive mechanism for driving the plate between a first position in which the hole is at the first location and a second position in which the hole is at the second location.

30 Claims, 17 Drawing Sheets

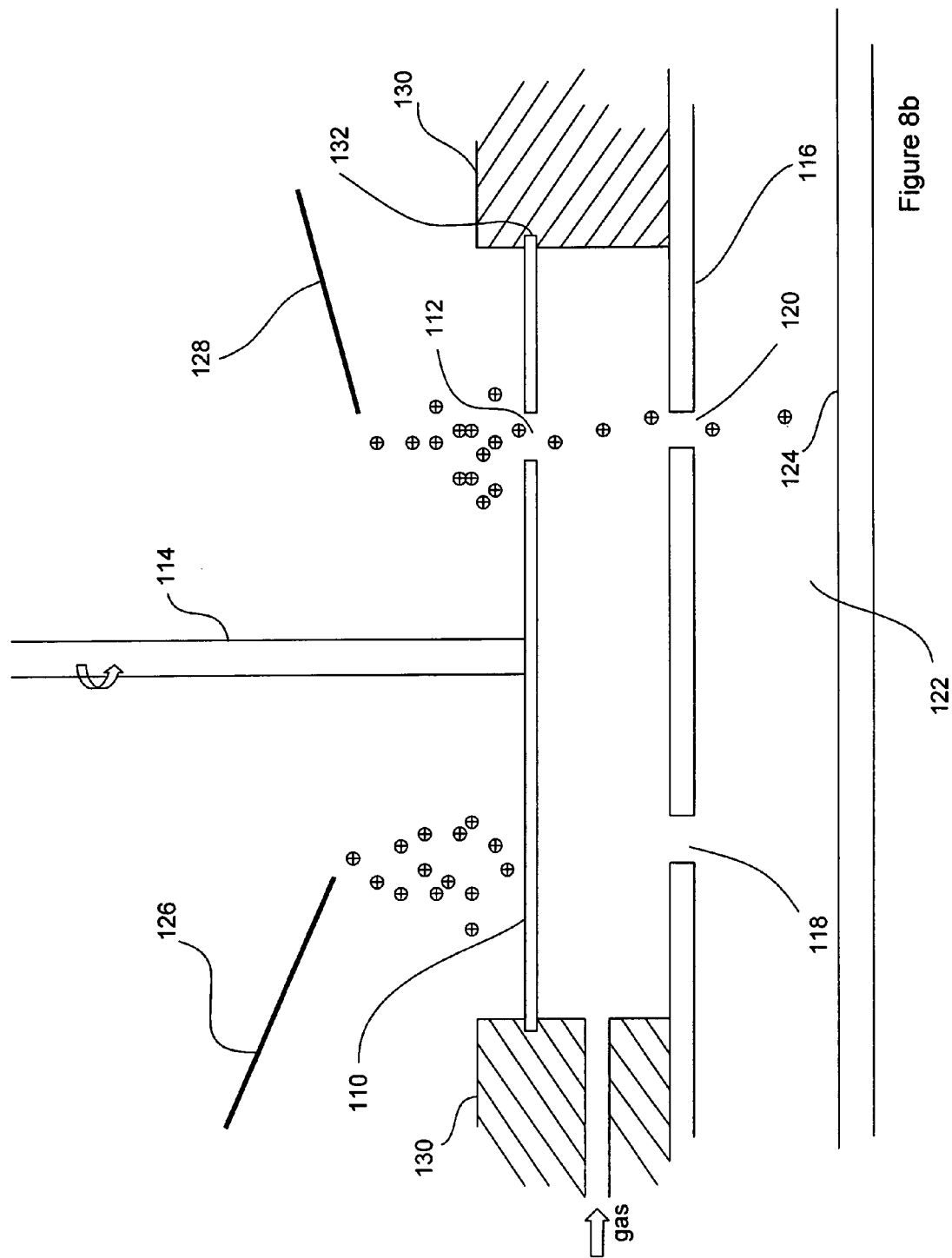

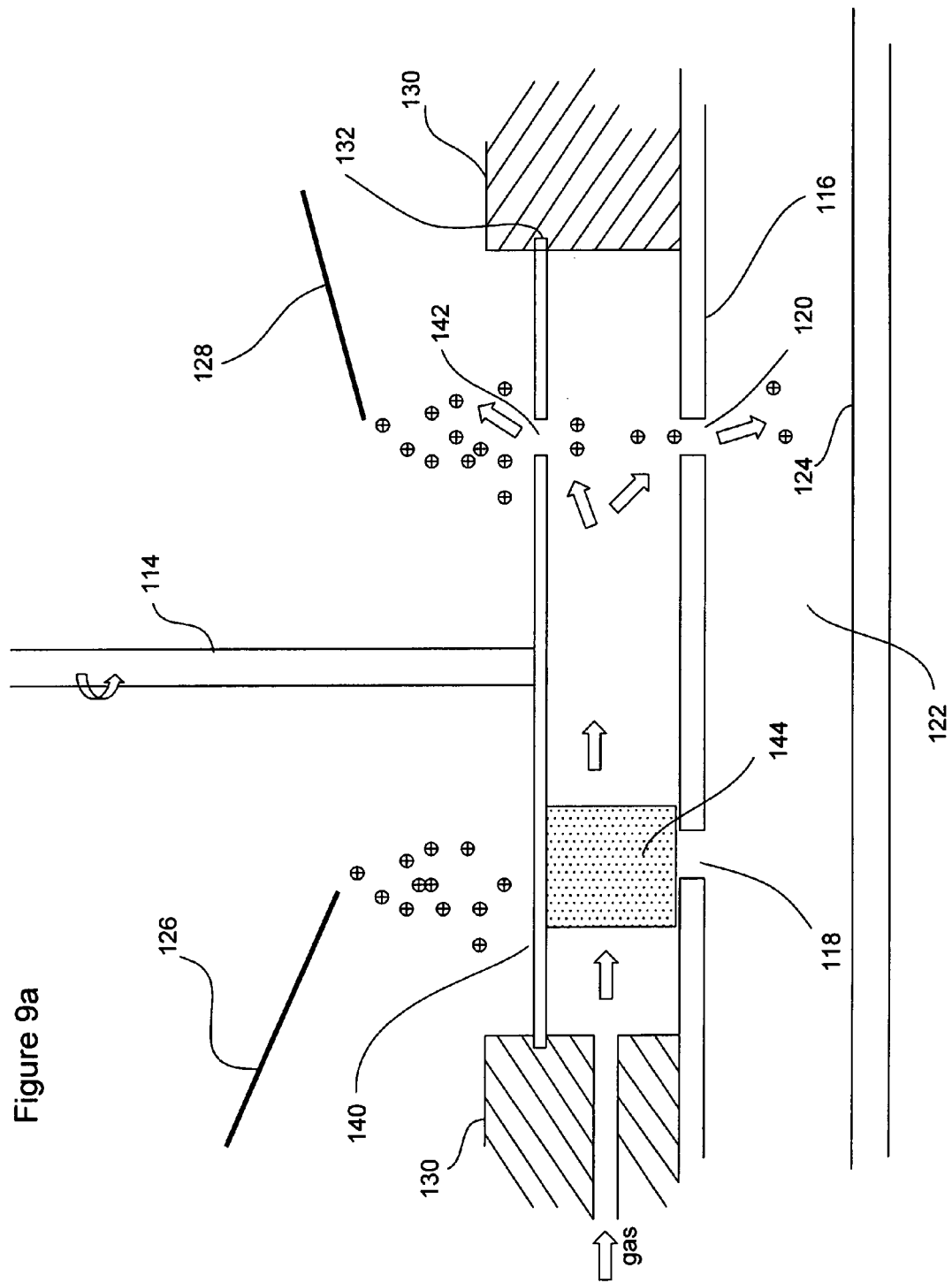

METHOD AND APPARATUS FOR SELECTING INLETS OF A MULTIPLE INLET FAIMS

This application claims benefit from U.S. Provisional application 60/549,170 filed on Mar. 3, 2004.

FIELD OF THE INVENTION

This invention relates generally to High-Field Asymmetric Waveform Ion Mobility Spectrometry (FAIMS) and more particularly to a selection system for multiple inlet FAIMS.

BACKGROUND OF THE INVENTION

In an analytical instrument that includes an ionization source such as for example electrospray ionization (ESI), an atmospheric pressure gas phase ion separator such as for example a high-field asymmetric waveform ion mobility spectrometer (FAIMS), and a detection system such as for example mass spectrometry (MS), it is advantageous to provide samples to the system in parallel. This allows the analytical instrument to rapidly sequence from measurements made from a first sample delivery system (HPLC for example) and from a second delivery system (preferably, but not necessarily of a type identical to the first). If the detection system is fast compared to the delivery system, then it is advantageous to multiplex a plurality of input streams to the same detector.

Multiplexing a plurality of input streams to the same detector has been attempted using a combination of ESI and MS, but such a combination is generally not very practical because the mass spectrometer is not amenable to having multiple inlets into the vacuum system. At best, the resulting gas flow into each inlet is lower than that of one opening, but more importantly the ion optics system in the vacuum system is not generally designed to accommodate ions coming from more than one ion pathway. Two or more inlets to the same MS is desirable, but is not generally practical.

Commercial systems for permitting two or more electrospray sources to operate in conjunction with one orifice into a mass spectrometer have been described. Most notable of these systems is the Micromass™ system for LockSpray™. Using the LockSpray™ system, a time-of-flight (TOF) mass spectrometer (for example) is re-calibrated intermittently during a measurement by moving a small baffle that temporarily prevents ions from an analytical source of sample from entering the MS vacuum system, whilst permitting ions from a second reference LockMass™ electrospray needle to enter the MS and be detected. Once the calibration using the reference LockMass™ compound is completed, the baffle is returned to its original position to permit the ions from the analytical ESI needle to continue to enter the MS and be measured.

If one inlet to FAIMS is used, all of the existing technology applicable to single orifice mass spectrometers would appear to be applicable. However, since FAIMS operates at atmospheric pressure, ions optionally are introduced via multiple inlets. A version of FAIMS with openings around the circumference of the outer electrode have been described previously, such as for instance in U.S. Pat. No. 6,753,522 which issued on Jun. 22, 2004 in the name of Guevremont et al., the entire contents of which are incorporated herein by reference. The ions originating from one of a plurality of ESI sources are selected by moving a ring version of the curtain plate around the FAIMS such that a single opening in the ring is situated in front of each opening in turn. However, the ring-shaped electrode is mechanically very difficult and inconvenient to actuate in an automated manner. In addition, the ring-shaped electrode does not readily support introduction of ions from different ionization sources via inlet orifices that are disposed at different positions along the length of the FAIMS analyzer.

It would be advantageous to provide a system and method for introducing ions into a FAIMS analyzer that overcomes at least some of the above-mentioned disadvantages of the prior art.

SUMMARY OF THE INVENTION

It is an object of at least some of the embodiments of the instant invention to provide ions from one ESI source to FAIMS through an active or open orifice, whilst preventing ions from another ESI source from entering FAIMS through a non-active or covered orifice.

It is also an object of at least some of the embodiments of the instant invention to provide a multi-inlet FAIMS that mimics relatively closely the physical arrangement of ESI ion sources.

It is also an object of at least some of the embodiments of the instant invention to provide an inlet selector system that supports selection of two or more inlets to FAIMS that are in close proximity to each other.

According to an aspect of the instant invention, provided is an apparatus for separating ions, comprising: a first electrode; a second electrode disposed in a spaced-apart relationship with the first electrode, a space between the first electrode and the second electrode defining a FAIMS analyzer region therebetween, the FAIMS analyzer region in fluid communication with an ion outlet orifice; a first ion inlet orifice defined within a first portion of the first electrode such that ions introduced via the first ion inlet orifice travel a first distance between the first ion inlet orifice and the ion outlet orifice; a second ion inlet orifice defined within a second portion of the first electrode such that ions introduced via the second ion inlet orifice travel a second distance between the second ion inlet orifice and the ion outlet orifice, the second distance being shorter than the first distance; and, an ion inlet orifice selector comprising a selector electrode having an opening defined therethrough, the selector electrode moveable between a first position in which the opening is aligned with the first ion inlet orifice for supporting introduction of a flow of ions into the FAIMS analyzer region via the first ion inlet orifice and a second position in which the opening is aligned with the second ion inlet orifice for supporting introduction of a flow of ions via the second ion inlet orifice.

According to another aspect of the instant invention, provided is a method for separating ions, comprising: providing a FAIMS analyzer region in fluid communication with an ion detector; providing a first ionization source in communication with a sample material including a precursor of an ion type of interest; providing a second ionization source in communication with a sample material including the precursor of the ion type of interest; using the first ionization source, producing a mixture of ions comprising different types of ions including the ion type of interest; during a first period of time, directing the ions from the first ionization source along a path of a first length through the FAIMS analyzer region, the first length being sufficient to effect at least a partial separation of the ion type of interest from other types of ions in the mixture; using the ion detector, detecting ions after the ions have traveled the first length; using the second ionization source, producing a mixture of ions comprising different types of ions including the ion type of interest; during a second period of time not overlapping with the first period of time, directing the ions from the second ionization source along a path of a second length through the FAIMS analyzer region, the second length being insufficient to effect a separation of the ion type of interest from other types of ions in the mixture to a same extent as occurs along the path of the first length; using the ion detector, detecting ions after the ions have traveled the second length.

According to another aspect of the instant invention, provided is a method for separating ions, comprising: providing a FAIMS analyzer region in fluid communication with an ion detector; introducing a mixture of different types of ions including an ion type of interest into the analyzer region via a first ion inlet orifice; selectively transmitting the ion type of interest through the analyzer region and to the ion detector; introducing ions of a calibration compound into the analyzer region via a second ion inlet orifice, the second ion inlet orifice positioned for use in calibration; transmitting the ions of a calibration compound to the ion detector; and, in dependence upon a response of the ion detector to the ions of a calibration compound, modifying at least one operational parameter of the ion detector.

According to another aspect of the instant invention, provided is a method for separating ions, comprising: providing a FAIMS analyzer region in fluid communication with a mass spectrometric ion detector; providing a first ionization source in communication with a sample material including a precursor of an ion type of interest; providing a second ionization source in communication with a material including a precursor of a LockMass ion; using the first ionization source, producing a mixture of ions comprising different types of ions including the ion type of interest; using the second ionization source, producing LockMass ions from the precursor of the LockMass ion; during a first period of time, aligning an opening of a selector electrode between the second ionization source and a first ion inlet into the FAIMS analyzer region; during the first period of time, directing the LockMass ions from the second ionization source into the FAIMS analyzer region and transmitting the LockMass ions to the mass spectrometric ion detector; detecting the LockMass ions and determining the mass-to-charge ratio of the LockMass ions; calibrating the mass-scale in dependence upon a difference between the determined mass-to-charge ratio of the LockMass ions and an expected mass-to-charge ratio of the LockMass ions; during a second period of time not overlapping with the first period of time, aligning the opening of the selector electrode between the first ionization source and a second ion inlet into the FAIMS analyzer region; during the second period of time, directing the ions from the first ionization source into the FAIMS analyzer region and selectively transmitting the ion type of interest to the mass spectrometric ion detector; and, detecting the ion type of interest using the mass spectrometric ion detector and determining the mass-to-charge ratio of the ion type of interest.

BRIEF DESCRIPTION OF THE DRAWINGS

Exemplary embodiments of the invention will now be described in conjunction with the accompanying drawings, in which:

FIG. 8b shows the system of FIG. 7 in a second mode of operation;

FIG. 9a shows a cross sectional view of an ion introduction region of a system according to another embodiment of the instant invention, in a first mode of operation;

DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
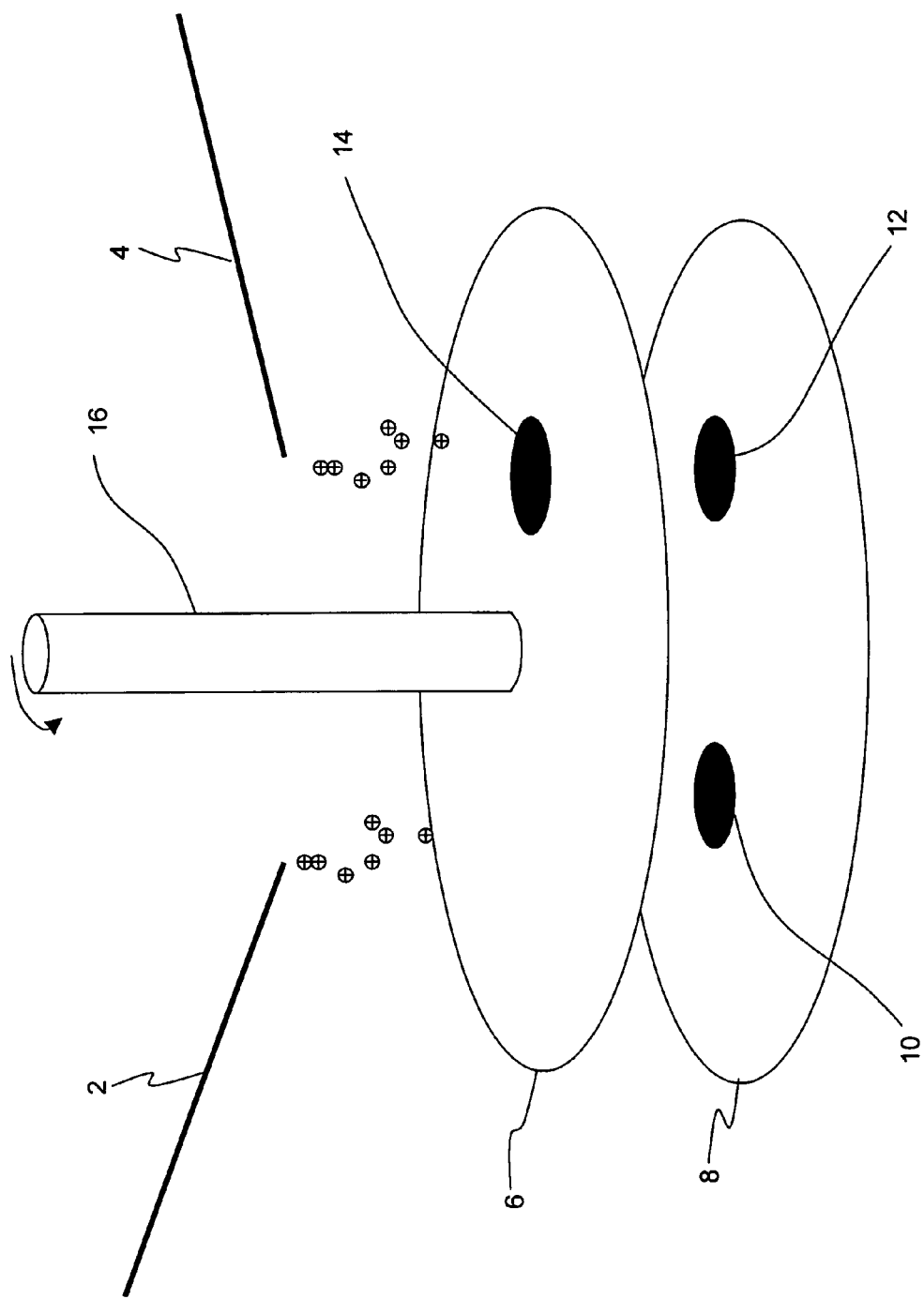
FIG. 1 shows a side view of a single-hole selector electrode according to an embodiment of the instant invention.

FIG. 1 is a schematic diagram that shows two atmospheric pressure ionization sources, in the form of a first electrospray needle 2 and a second electrospray needle 4, spraying ions toward a single-hole selector electrode 6 that is positioned adjacent and parallel to a lower plate 8 which has two openings 10 and 12 defined therethrough. Lower plate 8 with the two openings 10 and 12 is a portion of one of a curtain plate and an outer electrode of a not illustrated FAIMS analyzer. Both cases will be considered in greater detail, below. The single-hole selector electrode 6 includes a single opening 14 defined therethrough and is mounted to a drive shaft 16.

Figure 2A:
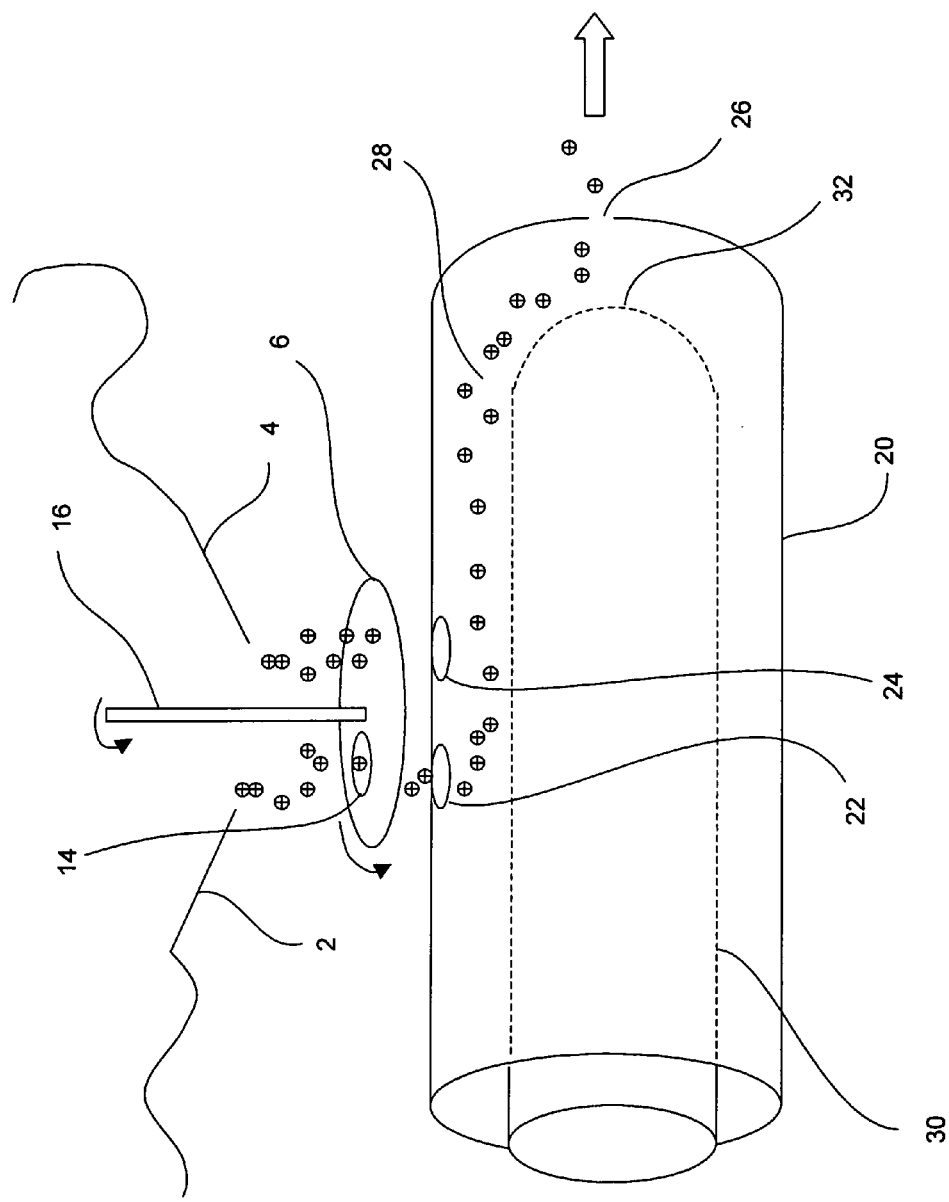
FIG. 2a is a schematic diagram of a single-hole selector electrode disposed adjacent and parallel to an outer electrode of a FAIMS analyzer, in a condition for introducing ions via a first ion inlet orifice.

Referring now to FIG. 2a, shown is a single-hole selector electrode disposed adjacent and parallel to an outer electrode of FAIMS. Elements labeled with the same numerals have the same function as those illustrated in FIG. 1. In FIG. 2a, the outer electrode 20 of FAIMS has two ion inlet orifices 22 and 24 defined therethrough and also defines an ion outlet orifice 26. An analyzer region 28 is defined by a space between the outer electrode 20 and an inner electrode 30 of the FAIMS. The inner electrode 30 includes a domed terminus 32 for directing ions along an average ion flow path within the analyzer region 28 that passes outwardly through the ion outlet orifice 26.

In the system shown in FIG. 2a, both the first electrospray needle 2 and the second electrospray needle 4 are in continuous operation. The opening 14 is the single-hole selector electrode 6 is controllably alignable with the first ion inlet orifice 22 or the second ion inlet orifice 24 by rotation of the single-hole selector electrode 6 about a rotation axis aligned with the drive shaft 16. For instance, a not illustrated motor or the other mechanical device actuates the drive shaft 16 to rotate the single-hole selector electrode 6 to adopt one of two possible rotational orientations. In each orientation the single opening 14 is positioned adjacent to one of the ion inlet orifices 22 and 24 into FAIMS. By positioning this selector electrode, the user has the option of introducing ions from either, but not both, ion sources 2 and 4 into the FAIMS system at a time.

Referring still to FIG. 2a, the opening 14 is positioned to allow ions from the first electrospray needle 2 to pass into the analyzer region 28. Accordingly, a mixture of ions including different types of ions including an ion type of interest is introduced into the analyzer region 28 in FIG. 2a. The ions of the mixture are separated according to the FAIMS principle as they traverse the analyzer region 28, and the ions passing out of FAIMS vie the ion outlet orifice 26 are enriched in the ion type of interest. Types of ions other than the ion type of interest are selectively lost as a result of collisions with an electrode surface of the FAIMS. Ions produced by a second ionization source 4 impinge upon the single-hole selector electrode 6 at a point away from the opening 14 and are neutralized. Accordingly, in FIG. 2a ions from the second ionization source 4 do not enter the FAIMS analyzer region 28.

Figure 2B:
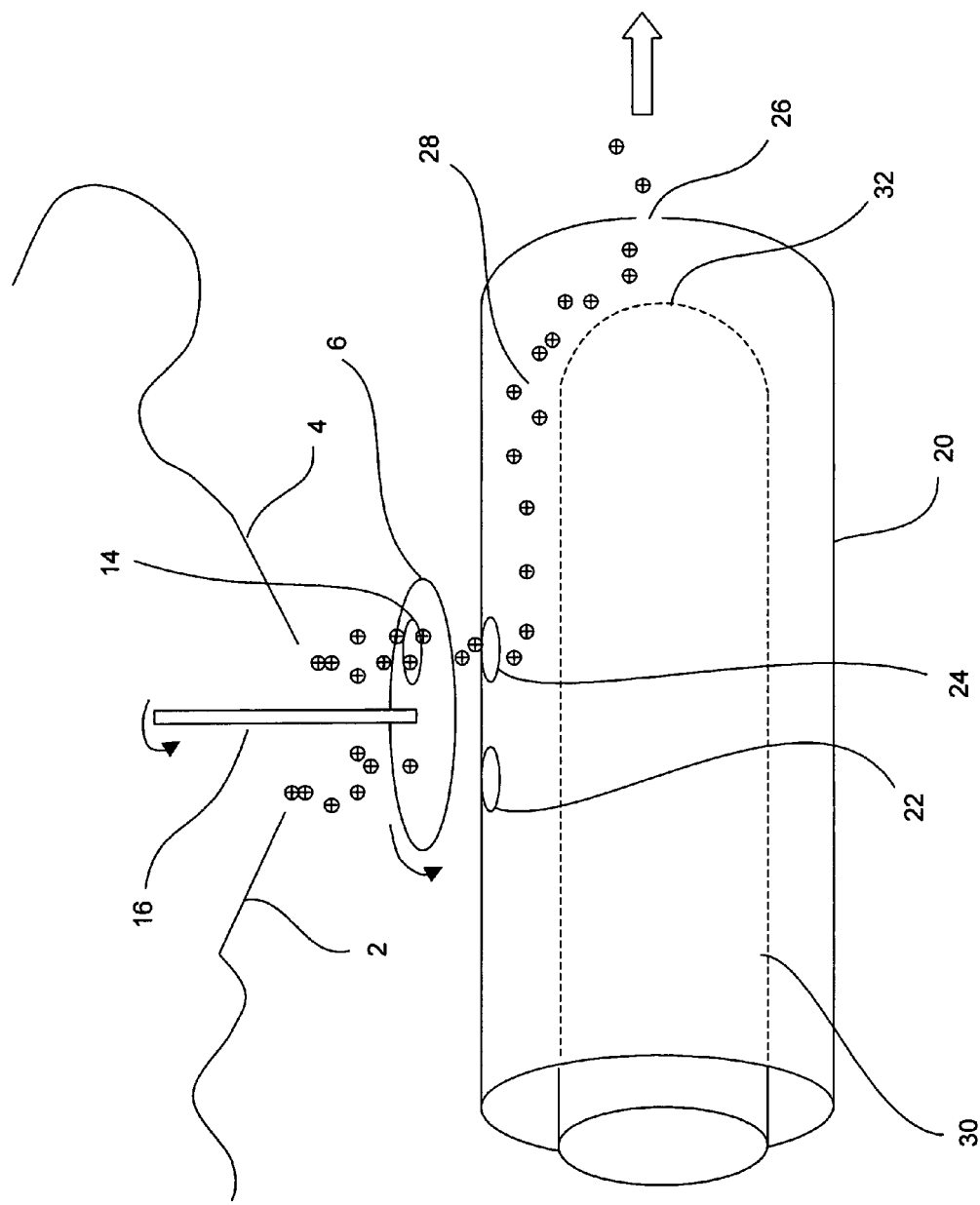
FIG. 2b is a schematic diagram of a single-hole selector electrode disposed adjacent and parallel to an outer electrode of a FAIMS analyzer, in a condition for introducing ions via a second ion inlet orifice.

Referring now to FIG. 2b, shown is the system of FIG. 2a but with the opening 14 positioned to allow ions from the second electrospray needle 4 to pass into the analyzer region 28. Accordingly, a mixture of ions including different types of ions including an ion type of interest is introduced into the analyzer region 28 in FIG. 2b. The ions of the mixture are separated according to the FAIMS principle as they transverse the analyzer region 28, and the ions passing out of FAIMS via the ion outlet orifice 26 are enriched in the ion type of interest. Types of ions other than the ion type of interest are selectively lost as a result of collisions with an electrode surface of the FAIMS. Ions produced by the first ionization source 2 impinge upon the single-hole selector electrode 6 at a point away from the opening 14 and are neutralized. Accordingly, in FIG. 2b ions from the first ionization source 2 do not enter the FAIMS analyzer region 28.

Advantageously, the system shown at FIGS. 2a and 2b supports rapid sequencing between different ionization sources and/or different samples. For instance, optionally the ion type of interest produced by the first ionization source 2 and the ion type of interest produced by the second ionization source 4 are different types of ions. Further optionally, the first ionization source 2 and the second ionization source 4 are different types of ionization sources. Still further optionally, the sample is provided to each of the first ionization source 2 and the second ionization source after separation using a chromatographic or electrophoretic technique. For instance, the first ionization source 2 is in communication with an outlet of a HPLC system and the second ionization source is in communication with the outlet of a GC system. Advantageously, sample eluted from one of the HPLC system and GC system may be analyzed using the FAIMS system during a time of no sample elution from the other one of the HPLC system and the GC system. Since analysis by chromatographic or electrophoretic techniques is characterized by long periods of separation followed by a relatively short elution period, multiplexing several chromatographic or electrophoretic systems into a single FAIMS with rapid switching between sources is efficient.

Figure 3A:
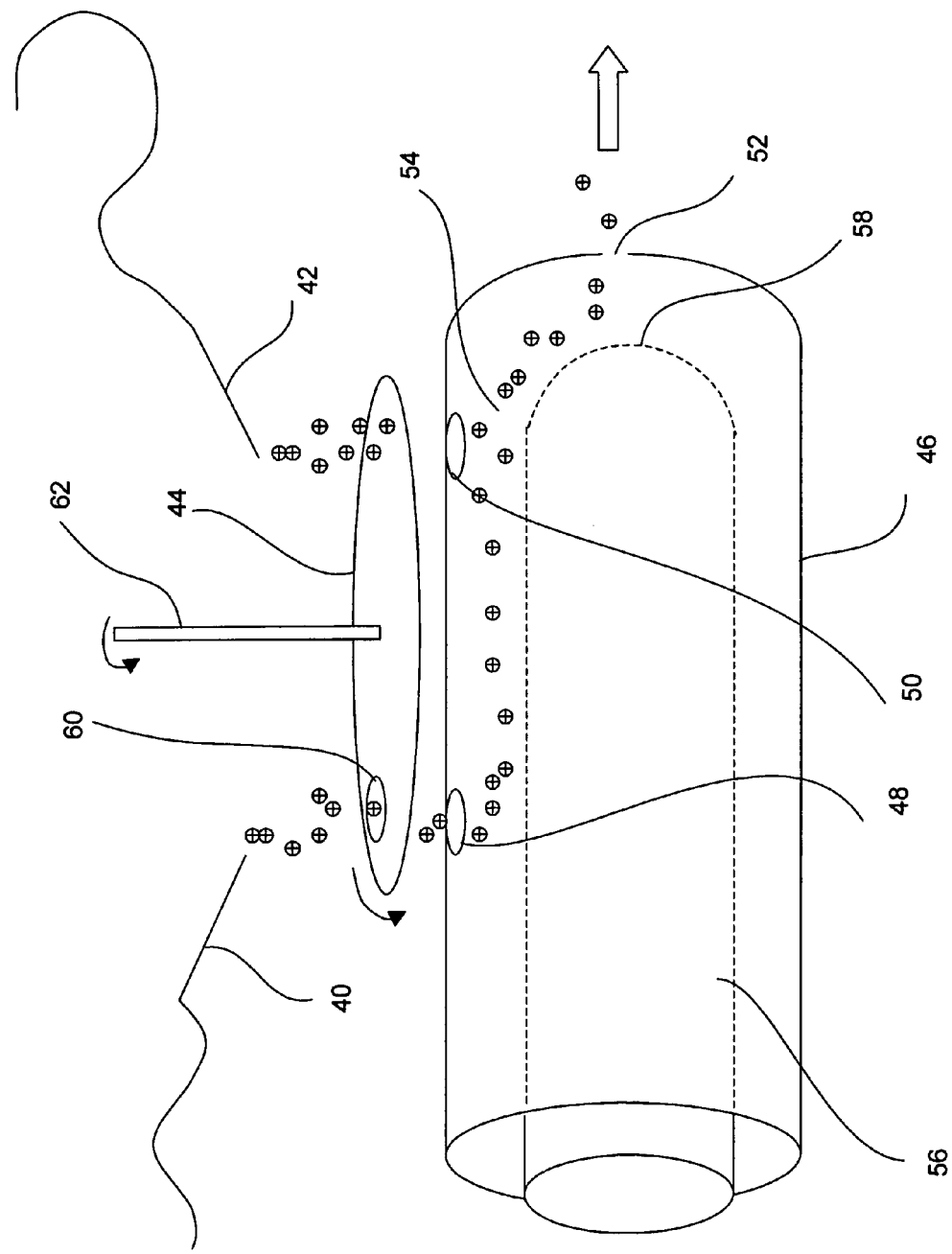
FIG. 3a is a schematic diagram of a single-hole selector electrode disposed adjacent and parallel to an outer electrode of a FAIMS analyzer, in a condition for selectively introducing ions in a FAIMS separation mode via a first ion inlet orifice into the FAIMS analyzer.
Figure 3B:
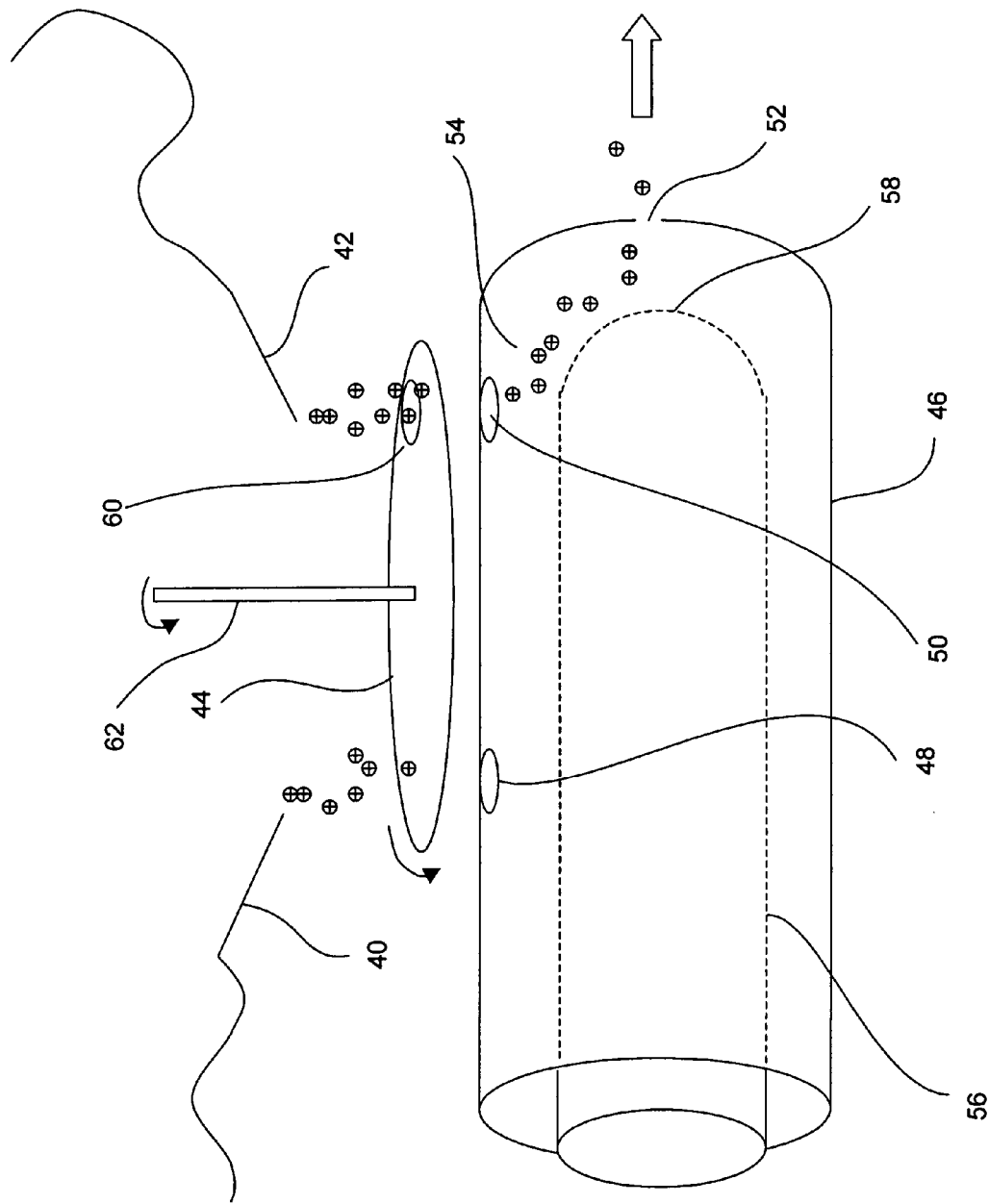
FIG. 3b is a schematic diagram of a single-hole selector electrode disposed adjacent and parallel to an outer electrode of a FAIMS analyzer, in a condition for selectively introducing ions in a total ion mode via a second ion inlet orifice into the FAIMS analyzer.

Referring now to FIGS. 3a and 3b, shown is a single-hole selector electrode disposed adjacent and parallel to an outer electrode of FAIMS. The system shown at FIGS. 3a and 3b is a special case of the system that was described with reference to FIGS. 2a and 2b, above. Two atmospheric pressure ionization sources, in the form of a first electrospray needle 40 and a second electrospray needle 42, are disposed for spraying ions toward a single-hole selector electrode 44 that is positioned adjacent and parallel to an outer electrode 46 of FAIMS. Two ion inlet orifices 48 and 50 are defined through the outer electrode 46. The outer electrode 46 also defines and ion outlet orifice 52. An analyzer region 54 is defined by a space between the outer electrode 46 and an inner electrode 56 of the FAIMS. The inner electrode 56 includes a domed terminus 58 for directing ions along ion flow path within the analyzer region 54 that passes outwardly through the ion outlet orifice 52.

Referring still to FIGS. 3a and 3b, the first ion inlet orifice 48 is defined within a first portion of the outer electrode 46 such that ions introduced via the first ion inlet orifice 48 travel a first distance between the first ion inlet orifice 48 and ion outlet orifice 52. In particular, the first distance is selected to provide an average ion flow path through the analyzer region 54 that is sufficiently long to support at least partial separation of a first type of ion contained in a mixture of ions introduced via the first ion inlet orifice 48, from a second type of ion contained in the same mixture. In other words, ions introduced into the analyzer region 54 via the first ion inlet orifice 48 are separated according to the FAIMS principle. Conversely, the second ion inlet orifice 50 is defined within a second portion of the outer electrode 46 such that ions introduced via the second ion inlet orifice 50 travel a second distance between the second ion inlet orifice 50 and the ion outlet orifice 52, the second distance being shorter than the first distance. In particular, the second distance is selected to provide an average ion flow path through the analyzer region 54 that is sufficiently short to support transmission of plural types of ions contained in a mixture of ions introduced via the second ion inlet orifice 50. Optionally by removing the asymmetric waveform and compensation voltage difference between the FAIMS electrodes, and by providing a short ion path, the FAIMS separation mechanism is effectively "turned off" for those ions introduced into the analyzer region 54 via the second ion inlet orifice 50.

Referring still to FIGS. 3a and 3b, both the electrospray needle 40 and the second electrospray needle 42 are in continuous operation. An opening 60 in the single-hole selector electrode 44 is selectably alignable with the first ion inlet orifice 48 or the second ion inlet orifice 50 by rotation of the single-hole selector electrode 44 about a rotation axis aligned with drive shaft 62. For instance, a not illustrated motor or other mechanical device actuates the drive shaft 62 to rotate the single-hole selector electrode 44 to adopt one of two possible rotational orientations. In each orientation the opening 60 is positioned adjacent to one of the ion inlet orifices in FAIMS. By positioning this selector electrode, the user has the option of permitting ions from either, but not both, ion sources 48 and 50 to enter the FAIMS system.

One non-limiting example of an application for the system that is shown in FIGS. 3a and 3b is for supporting a "total ion" mode of operation with the electric fields removed, and optionally a partial-separation FAIMS mode of operation without the need for changing electric field conditions within the FAIMS analyzer region 54. Another non-limiting example of an application for the system that is shown in FIGS. 3a and 3b for supporting use of a Lock-Mass™ or other calibration compound.

In the "total ion" mode of operation both the first electrospray needle 40 and the second electrospray needle 42 are producing ions from a same sample material. As is shown at FIG. 3a, when the opening 60 of the single-hole selector electrode 44 is aligned with the first ion inlet orifice 48, a mixture of ions is introduced via the first ion inlet orifice 48 and some types of ions are selectively transmitted through the analyzer region 54 to the ion outlet orifice 52. For a particular combination of applied asymmetric waveform and compensation voltages, only one or a relatively few types of ions are expected to be transmitted between the first ion inlet orifice 48 and the ion outlet orifice 52. However, when as is shown at FIG. 3b the opening 60 of the single-hole selector 44 is aligned with the second ion inlet orifice 50, a mixture of ions is introduced via the second ion inlet orifice 50. In this second orientation of the selector electrode, the voltages applied to the FAIMS electrodes are optionally removed, and may be replaced with voltages that result in very low electric fields in the analyzer region. Since the distance between the second ion inlet orifice 60 and ion outlet 52 is short, substantially all types of ions are transmitted between the second ion inlet orifice 50 and the ion outlet orifice 52. Optionally, the applied asymmetric waveform and compensation voltages may remain applied. In this case some separation will proceed, but with limited effectiveness because of the short distance between the second ion inlet orifice 50 and the ion outlet orifice 52.

Another non-limiting example of an application for the system that is shown in FIGS. 3a and 3b is for supporting use of a LockMass™ or other calibration compounds. This operation is required in specialized situations where very high mass resolution is needed. The calibration sample may contain precursor chemicals to provide one or more ions of known mass-to-charge (m/z) ratio so that the mass spectrometer mass-scale may be corrected regularly. Because of small physical changes inside the mass spectrometer the mass-scale may be highly accurate for limited periods of time, are therefore the mass-scale requires small refinements on a regular bases during the time when other types of ions of interest are being analyzed. When it is desired that ions of a LockMass™ compound be provided for purposes of calibration, then the single-hole selector electrode 44 is aligned with the second ion inlet orifice 50 to support introduction of LockMass™ from the second electrospray needle 42. Since the LockMass™ compound can be provided at relatively high abundance, it is advantageous to be able to transmit the LockMass™ ions along a flow path through the analyzer region 54 that is short compared to a flow path for separating ions. In this way, the LockMass™ ions are introduced and pass through the FAIMS analyzer region 54 to a not illustrated mass spectrometer very rapidly. A delay time associated with the ions passing through a longer portion of the analyzer region 54 is avoided.

In the systems shown at FIGS. 2a–3b, the flows of gas have been omitted for the sake of clarity. It is advantageous to provide a curtain gas between the single-hole selector electrode and the outer electrode of FAIMS. Optionally, a flow of a carrier gas is provided within the analyzer region between the inner and outer FAIMS electrodes, to carry the ions along a direction toward the ion outlet. Although electrospray sources have been shown in the figures, many other ion sources can be used in this system including, but not restricted to atmospheric pressure chemical ionization, corona discharge, radioactivity (Ni foil), laser or high energy photons (MALDI, photoionization). In use, electrical connections are made to each electrospray needle (or other ion source components), the rotating selector electrode, to the curtain plate and outer FAIMS electrode to form a voltage gradient to drive the ions from the electrospray needle into the FAIMS analyzer region. In the case of ESI, a strong electric field around the tip of the electrospray needle is required to produce a fine spray of liquid droplets, and the formation of ions. Typical voltages applied for production of positive ions would be: needles at about 3000 volts, the selector electrode at 1000 volts, the curtain plate slightly lower than 1000 and the outer electrode at close to zero volts respectively.

Figure 4A:
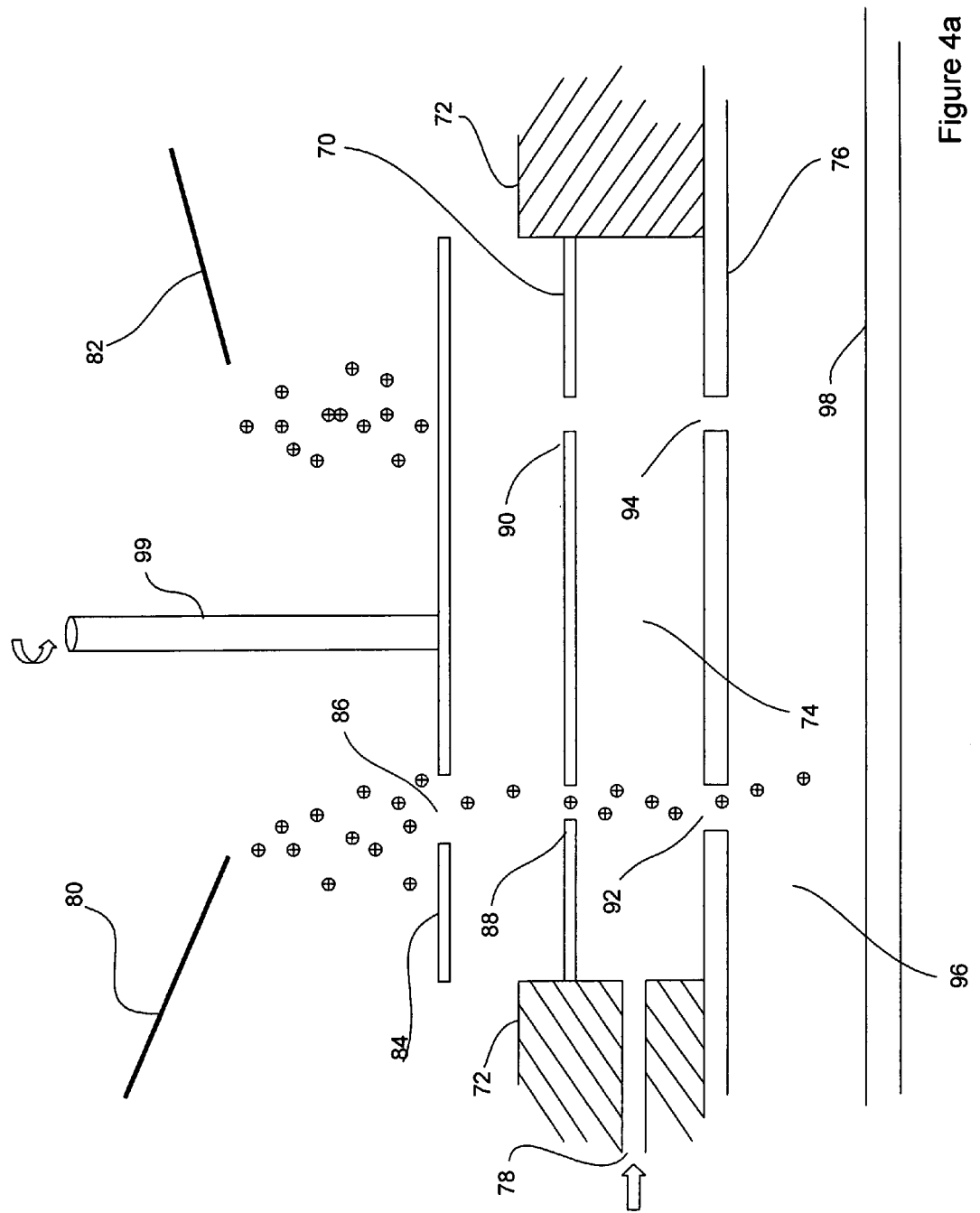
FIG. 4a shows an embodiment of the instant invention including both a rotating selector electrode and a curtain plate, in a first mode of operation.
Figure 4B:
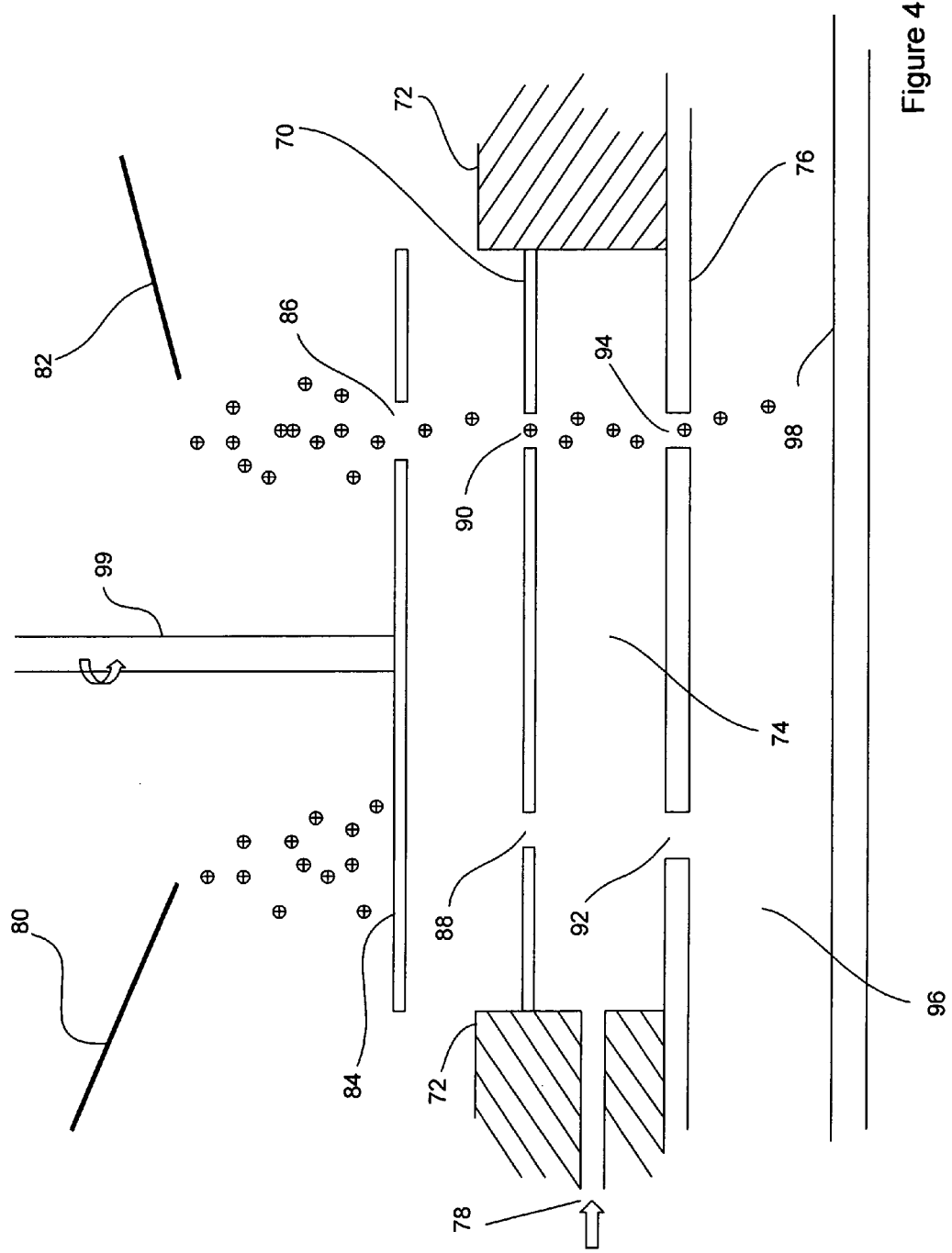
FIG. 4b shows an embodiment of the instant invention including both a rotating selector electrode and a curtain plate, in a second mode of operation.

Referring now to FIGS. 4a and 4b, shown is a system in which a single-hole selector electrode is disposed adjacent and parallel to a curtain plate of a FAIMS analyzer. The curtain plate 70 is mounted into gas tight connection with an insulator 72 that forms a chamber 74 between the curtain plate 70 and an upper electrode 76 of FAIMS. A flow of curtain gas 78 is delivered to the chamber 74. FIGS. 4a and 4b show ions being selected from one of a first electrospray needle 80 and a second electrospray needle 82, respectively, by rotation of a single-hole selector electrode 84 so that a single hole 86 in the single-hole selector electrode 84 is adjacent to one of the first electrospray needle 80 and second electrospray needle 82, respectively. For instance, a not illustrated motor or other mechanical device actuates a drive shaft 99 to rotate the single-hole selector electrode 84 to adopt one of two possible rotational orientations. By positioning the single-hole selector electrode 84, the user has the option of permitting ions from either, but not both, the first electrospray needle 80 and second electrospray needle 82 to enter the FAIMS system.

In the present embodiment, the single-hole selector electrode 84 is parallel and adjacent to the curtain plate 70, which has two orifices 88 and 90 defined therethrough. The upper electrode 76 of FAIMS also has two openings 92 and 94 defined therethrough and that are aligned with the orifices 88 and 90 in the curtain plate 70. When the three openings are aligned, for example when the single hole 86 in the single-hole selector electrode 84 is aligned with openings in the curtain plate 70 and the upper electrode 76 of FAIMS, the ions from the selected ionization source passes through the three co-aligned openings and into an analyzer region 96 of FAIMS between the upper electrode 76 and a lower electrode 98. The ions from the other non-selected source impinge on the surface of the single-hole selector electrode 84, and are discharged. It is advantageous that the ions from the non-selected source do not enter the FAIMS via the aligned openings adjacent to the selected source. Optionally, a blocking plate (not shown) is installed to prevent cross-talk between sources and openings. Advantageously the single-hole selector electrode 84 and the curtain plate 70 are in close proximity. The two may optionally be in sliding contact with each other. The single-hole selector electrode 84 and the curtain plate 70 are conductive electrodes connected to power supplies that are used to maintain the voltage applied to these electrodes. Similarly the upper electrode 76 of FAIMS is held at a bias voltage through contacts with a power supply.

Still referring to FIGS. 4a and 4b, a not illustrated portion of the curtain gas 78 flows outward through the curtain plate towards the ion source helping to desolvate the ions as they approach the curtain plate. A second (optional) portion of the gas 78 flows into FAIMS to contribute to (or constitute) the carrier gas that transports the ions through the analyzer region 96 of FAIMS. The flow of gases that are chosen is dependent on the type ion ionization source that is employed with the present invention. The gases discussed here are specific for the operation of an atmospheric pressure electrospray ionization system. Additionally, in some cases the source of ions may be operated at elevated or reduced temperatures, requiring isolation of FAIMS in order to operate FAIMS at optimum temperature for ion separation and ion transmission.

Figure 5:
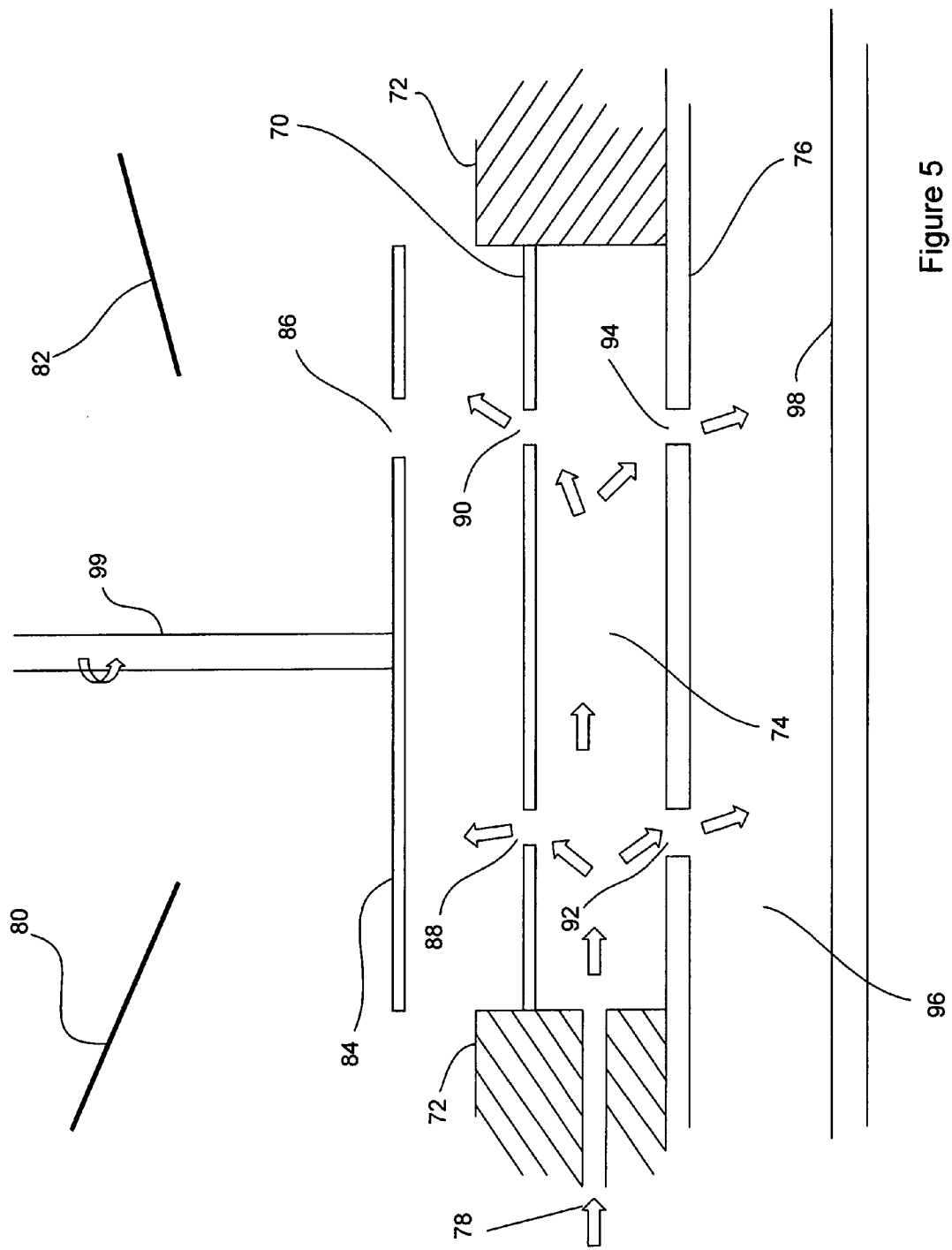
FIG. 5 shows patterns of the flow of gases supplied to the curtain region of the system of FIGS. 4a and 4b, when in the second mode of operation.

Referring now to FIG. 5, shown is the system of FIGS. 4a and 4b in which gas flows are illustrated but ions have been omitted for clarity. Elements labeled with the same numerals have the same function as those illustrated in FIGS. 4a and 4b. Since there are two openings 92 and 94 through the outer electrode 76 of FAIMS, a portion of the curtain gas optionally flows into each of these openings. The flow from the curtain region 74 into FAIMS through these two openings 92 and 94 optionally is reduced to approximately zero by providing a carrier gas to the analyzer region 96 independently. However, it is often found that the transmission of ions into the FAIMS analyzer is more efficient if a flow of gas aids transport of the ions from the chamber 74 between the curtain plate 70 and outer electrode 76 and into FAIMS. The curtain gas preferably flows outward through both openings 88 and 90 in the curtain plate 70, as shown in FIG. 5. Optionally, the single-hole selector electrode 84 is in close proximity or in sliding contact (and at the same electrical potential) with the curtain plate 70, thus always covering one (or both) of the holes in the curtain plate 70. It is advantageous in this case to switch rapidly between the two positions, to minimize the disturbance in the gas flows when the two holes in the curtain plate are simultaneously closed.

Figure 6:
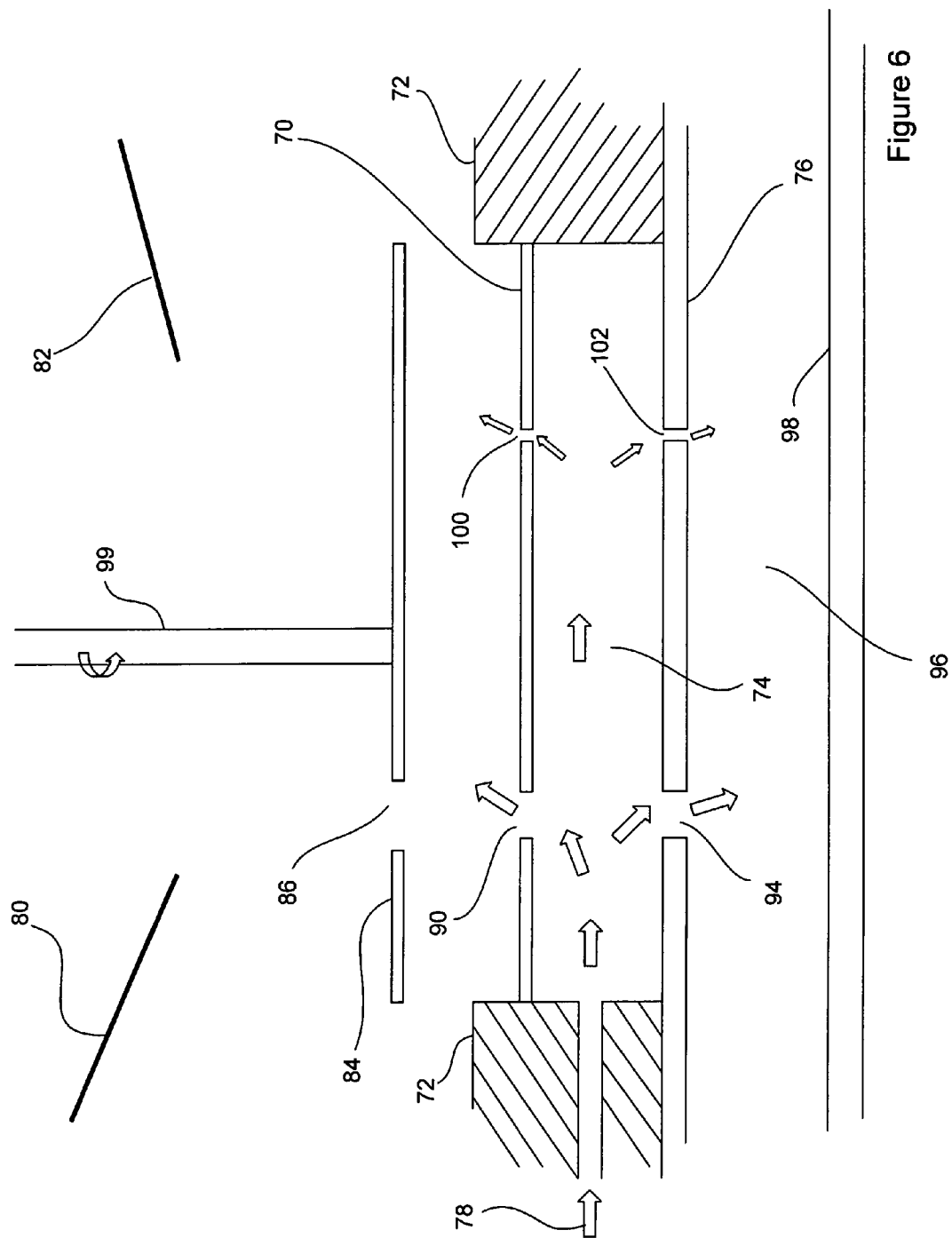
FIG. 6 shows the system of FIGS. 4a and 4b adapted for the special case of LockSpray™.

FIG. 6 illustrates the special case of LockSpray™ used with Waters high resolution TOF mass spectrometers. The first electrospray needle 80 is used to produce ions of the samples that are being analyzed, while the second electrospray needle 82 is used for producing ions of the calibration compound. In this LockSpray™ example, the ions from the second electrospray needle 82 are used for calibrating the mass-scale of the high resolution TOF mass spectrometer, and are passed only occasionally along a calibration channel through FAIMS for short periods of time to permit re-calibration of the mass spectrometer. It is therefore preferred that the opening 100 in the curtain plate 70 and the opening 102 in the outer electrode 76 of FAIMS are smaller for the calibration channel than the openings used for the analytical channel. Optionally, the number of ions of the calibration compound arriving at the detector is increased by increasing the concentration of the calibration compound delivered to second electrospray needle 82, thus minimizing the need for high sensitivity through use of large apertures through the curtain plate and outer electrode of FAIMS along the calibration channel.

Figure 7:
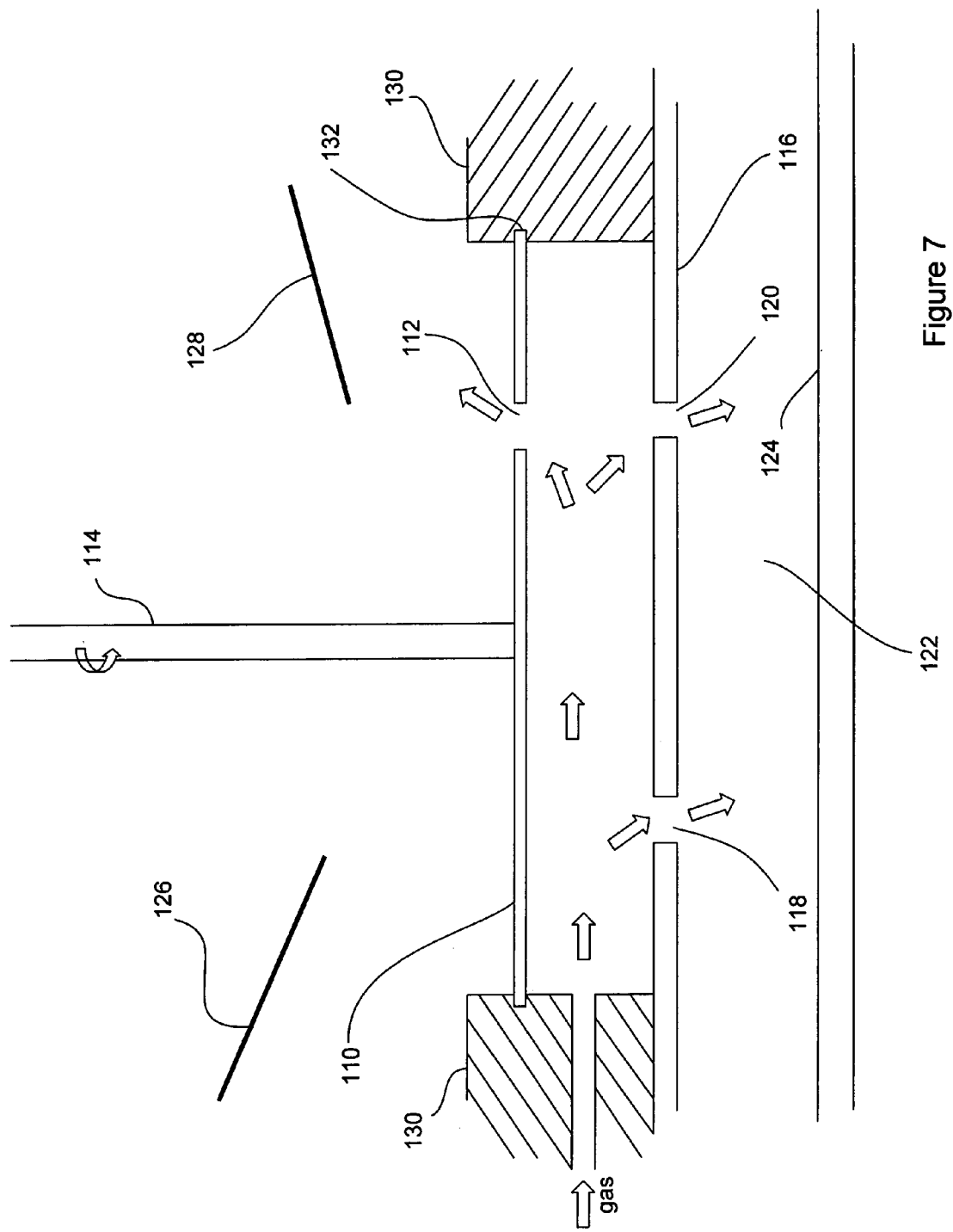
FIG. 7 shows a cross sectional view of an ion introduction region of a system according to another embodiment of the instant invention.

FIG. 7 illustrates in cross section an ion introduction region of a system according to an embodiment of the instant invention. In FIG. 7 a single-hole selector electrode 110 replaces the curtain plate 70 that is shown in FIGS. 4a through 6. The single-hole selector electrode 110 includes a single opening 112 defined therethrough and is mounted to a drive shaft 114. In FIG. 7, an upper electrode 116 of FAIMS has a first ion inlet orifice 118 and a second ion inlet orifice 120 defined therethrough. An analyzer region 122 is defined by a space between the upper electrode 116 and a lower electrode 124 of the FAIMS.

In the system that is shown at FIG. 7, both a first electrospray needle 126 and a second electrospray needle 128 are in continuous operation. The opening 112 in the single-hole selector electrode 110 is controllably alignable with the first ion inlet orifice 118 or the second ion inlet orifice 120 by rotation of the single-hole selector electrode 110 about a rotation axis aligned with the drive shaft 114. For instance, a not illustrated motor or other mechanical device actuates the drive shaft 114 to rotate the single-hole selector electrode 110 to adopt one of two possible rotational orientations. In each orientation the single opening 112 is positioned adjacent to one of the ion inlet orifices 118 and 120 into FAIMS. By positioning the single-hole selector electrode 110, the user has the option of introducing ions from either, but not both, ion sources 126 and 128 into the FAIMS system at a time.

Certain advantages result from substituting the curtain plate 70 of FIG. 6 with the single-hole selector electrode 110. For instance, the arrangement that is shown at FIG. 7 minimizes the total number of electrodes that are required. On the other hand, this approach requires that the single-hole selector electrode 110 remain in gas-tight contact with an electrically insulating material 130, as it smoothly rotates while driven by a drive shaft 114 and is used to select the source of ions to be delivered to FAIMS. To this end, the single-hole selector electrode 110 is retained about its periphery within a circumferential groove 132 that is defined within the electrically insulating material 130. The electrically insulating material 130 is disposed adjacent to the upper electrode 116 and forms a substantially gas-tight seal with the upper electrode 116, so as to define a curtain gas region proximate the first ion inlet orifice 118 and the second ion inlet orifice 120. In previous embodiments discussed above, the curtain plate 70 of FIG. 6 is a part of the gas-tight region into which curtain gas is delivered, and it is easier to maintain a gas-tight seal with a stationary, non-moving curtain plate 70.

It is a further advantage of the system shown at FIG. 7 that during rotation of the single-hole selector electrode 110, the gas flows are not disturbed. The three gas flows shown in FIG. 7, being two gas flows into the analyzer region of FAIMS via ion inlet orifices 118 and 120, and a flow through the single opening 112 of the selector electrode 110 towards the ionization sources, do not change during the rotation of the selector electrode 110. During the rotation, however, there is a period of time during which no ions enter the FAIMS analyzer. This delay is additive with a delay for ion transmission through the FAIMS to a not illustrated ion outlet.

Figure 8A:
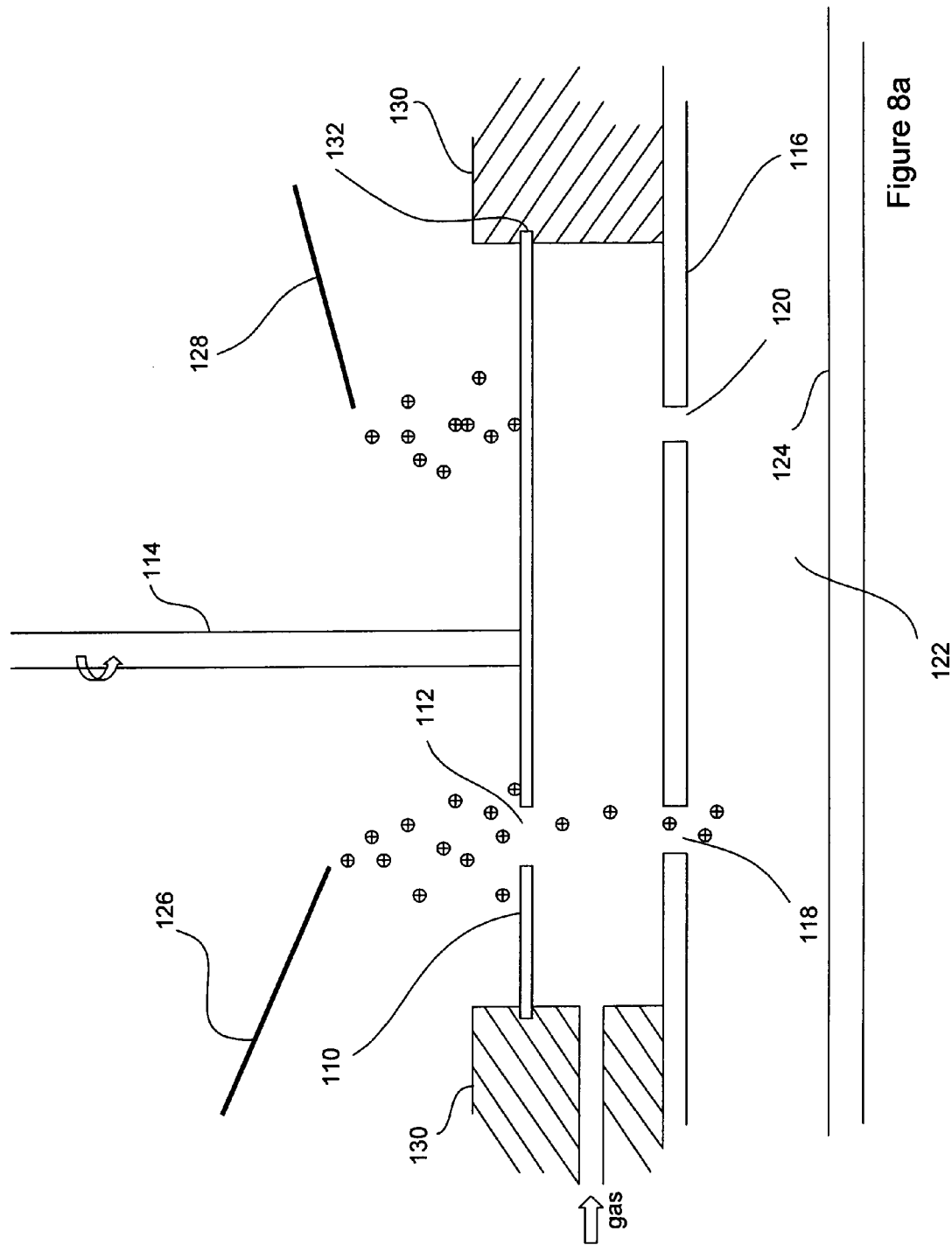
FIG. 8a shows the system of FIG. 7 in a first mode of operation.

FIGS. 8a and 8b illustrate the flow of ions through the system of FIG. 7 when the single-hole selector electrode 110 is aligned with the first ion inlet orifice 118 and the second ion inlet orifice 120, respectively. Elements labeled with the same numerals have the same function as those illustrated in FIG. 7. The periods of time at each of the two possible points of rotation, and the timing of the selection of each ion source is controlled from a master computer system (not shown).

Figure 9B:
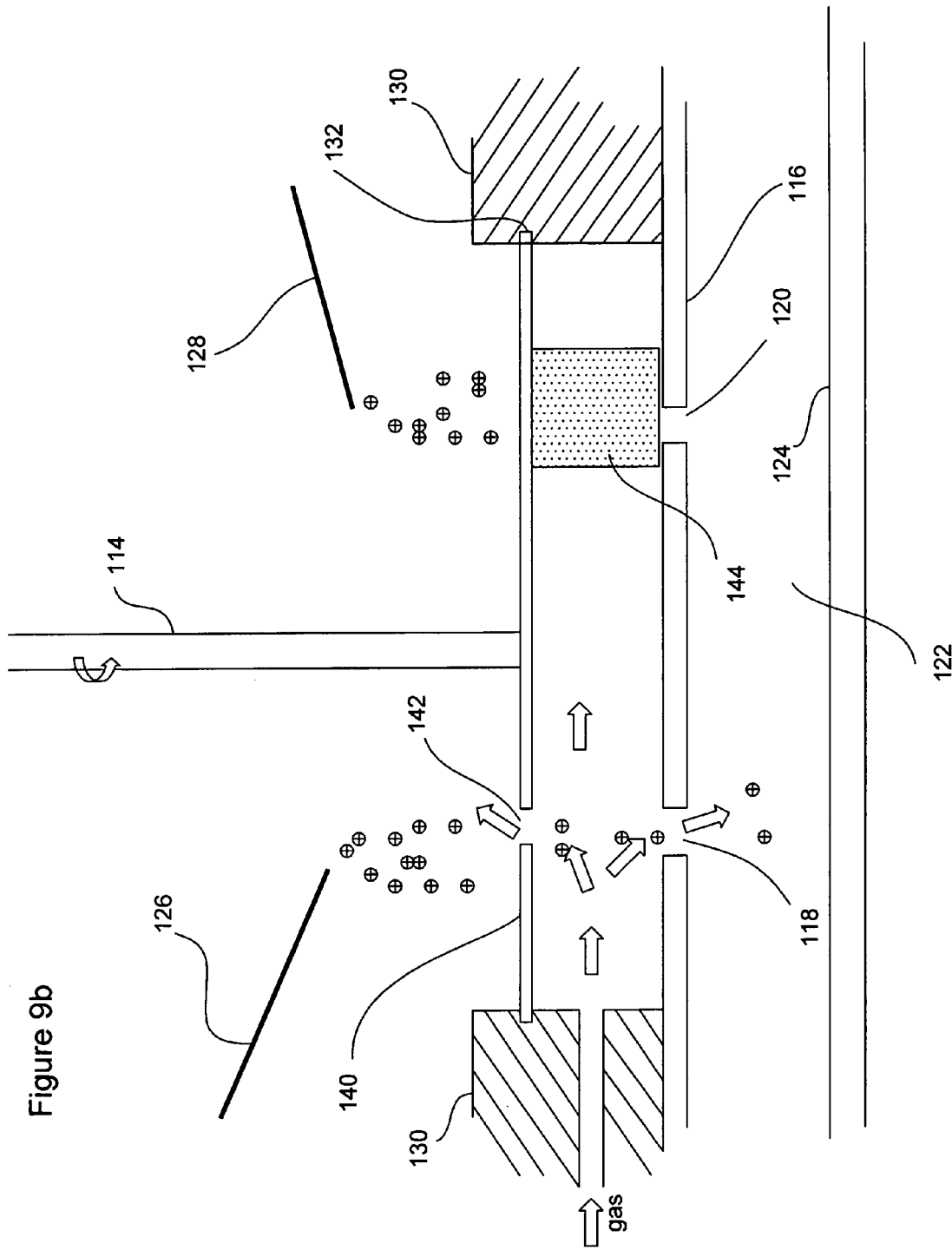
FIG. 9b shows the system of FIG. 9a in a second mode of operation.

FIGS. 9a and 9b show an ion introduction region similar to that discussed with reference to FIGS. 7 through 8b, but including a modified single-hole selector electrode. Elements labeled with the same numerals have the same function as those illustrated in FIGS. 7, 8a and 8b. In the present embodiment, a single-hole selector electrode 140 has an extension 144 from the surface facing the upper electrode 116 of FAIMS, which extension 144 serves to reduce or eliminate the flow of gas into the non-active orifice (e.g. the first ion inlet orifice 118 in FIG. 9a and the second ion inlet orifice 120 in FIG. 9b) in the upper electrode 116 of FAIMS. Of course, when the non-active orifice is covered by the extension 144, an active orifice (e.g. the second ion inlet orifice 120 in FIG. 9a and the first ion inlet orifice 118 in FIG. 9b) is aligned with an opening 142 in the single-hole selector electrode 140. Accordingly, in FIG. 9a ions from the second electrospray needle 128 are selectively passed into the FAIMS analyzer region 122 after passing through the opening 142 and the second ion inlet orifice 120. Similarly, in FIG. 9b ions from the first electrospray needle 126 are selectively passed into the FAIMS analyzer region 122 after passing through the opening 142 and the first ion inlet orifice 118.

The extension 144 is optionally a small disc of insulating material, such as for instance PEEK or Teflon™, that makes contact with the upper electrode 116 of FAIMS, so as to make gas-tight contact with the upper electrode 116 while covering one of the ion inlet orifices 118 and 120. The extension 144 is optionally a short cylinder only slightly wider in diameter than a larger one of the ion inlet orifices 118 and 120 (e.g. if one of the orifices 118 and 120 is dimensioned smaller than the other for LockMass™ applications), and therefore does not interfere substantially with the gas flow elsewhere in the region between the single-hole selector electrode 140 and the upper electrode 116 of FAIMS. If the extension 144 is a conductive material, electrical contact with the upper electrode 116 must be avoided. Optionally a small disc of insulator is mounted to the lower surface of the extension 144 to avoid electrical contact when the extension 144 is fabricated from a conductive material, and to provide complete closure of the opening in the upper electrode 116 of FAIMS. Since during use the pressure differences are small between the analyzer region and the curtain gas region, absolute gas-tight closure is not essential for significantly reducing the flow of gas through the non-active orifice in the upper electrode of FAIMS 116.

In the systems shown at FIGS. 4a to 9b, first ion inlet orifice is defined within a first portion of the upper FAIMS electrode such that ions introduced via the first ion inlet orifice travel a first distance between the first ion inlet orifice and an ion outlet orifice. In particular, the first distance is selected to provide an average ion flow path through the analyzer region of FAIMS that is sufficiently long to support at least partial separation of a first type of ion contained in a mixture of ions introduced via the first ion inlet orifice, from a second type of ion contained in the same mixture. In other words, ions introduced into the analyzer region of FAIMS via the first ion inlet orifice are separated according to the FAIMS principle. Optionally, the second ion inlet orifice is defined within a second portion of the upper electrode of FAIMS such that ions introduced via the second ion inlet orifice travel a second distance between the second ion inlet orifice and the ion outlet orifice, the second distance being shorter than the first distance. In particular, the second distance is selected to provide an average ion flow path through the analyzer region of FAIMS that is sufficiently short to support transmission of all types of ions contained in a mixture of ions introduced via the second ion inlet orifice. In this case, the FAIMS separation mechanism is effectively "turned off" for those ions introduced into the analyzer region via the second ion inlet orifice. Accordingly, this optional arrangement supports both a "total ion" mode of operation and use of a LockMass™ or other calibration compound, as described above with reference to FIGS. 3a and 3b.

Alternatively, the second ion inlet orifice is defined within a second portion of the upper electrode of FAIMS such that ions introduced via the second ion inlet orifice travel a second distance between the second ion inlet orifice and the ion outlet orifice. In this case, the second distance is shorter than the first distance but is sufficiently long to support at least partial separation of a first type of ion contained in a mixture of ions introduced via the second ion inlet orifice, from a second type of ion contained in the same mixture. Advantageously, this latter arrangement supports rapid sequencing between different ionization sources and/or different samples. For instance, optionally the ion type of interest produced by the first electrospray needle and the ion type of interest produced by the second electrospray are different types of ions. Further optionally, one of the first electrospray needle and the second electrospray needle is substituted by a different type of ionization source. Still further optionally, the sample is provided to each of the first electrospray needle and the second electrospray needle after separation using a chromatographic or electrophoretic technique. For instance, the first electrospray needle is in communication with an outlet of a HPLC system and the second electrospray needle is in communication with the outlet of a GC system. Advantageously, sample eluted from one of the HPLC system and the GC system may be analyzed using the FAIMS system during a time of no sample elution from the other one of the HPLC system and the GC system. Since analysis by chromatographic or electrophoretic techniques is characterized by long periods of separation followed by a relatively short elution period, multiplexing several chromatographic or electrophoretic systems into a single FAIMS with rapid switching between sources is efficient.

Furthermore, although the FAIMS of FIGS. 4a–9b was described in terms of an upper electrode and a lower electrode, such as for instance is found in a parallel plate geometry FAIMS, the description of the instant invention is equally applicable to other geometries of FAIMS, including but not limited to concentric cylinder geometry electrodes with or without a domed inner electrode; parallel plate geometry electrodes with either curved or flat electrode plates; concentric cylinder geometry electrodes operating in a side-to-side mode; spherical electrodes; quadrupolar electrodes; etc. In those geometries of the FAIMS device that are based upon overlapping concentric cylindrical electrodes, the upper electrode is equivalent to an outer cylindrical electrode and the lower electrode is equivalent to an inner cylindrical electrode.

All of the previous figures illustrate embodiments of the present invention wherein the ion sources are in close proximity to each other. This is advantageous since the mechanical means for opening and closing the openings for ion transmission into FAIMS can be relatively simple. This is also advantageous since the hardware holding the electrospray needles can be compact, and the ion sources may be enclosed within a common housing chamber (not shown here).

Figure 10B:
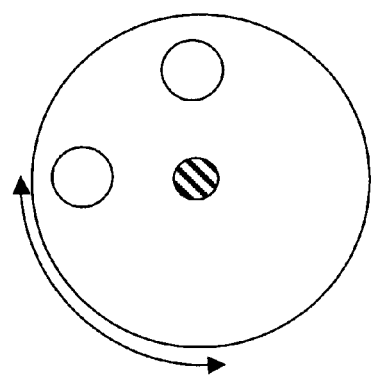
FIG. 10b shows a top view of a multiple-hole selector electrode.
Figure 10D:
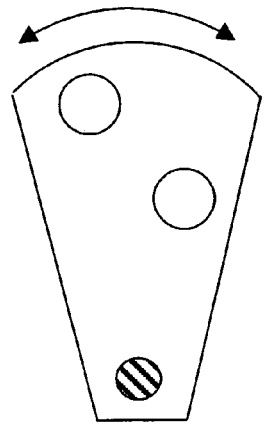
FIG. 10d shows a top view of an eccentrically mounted multiple-hole selector electrode.
Figure 10A:
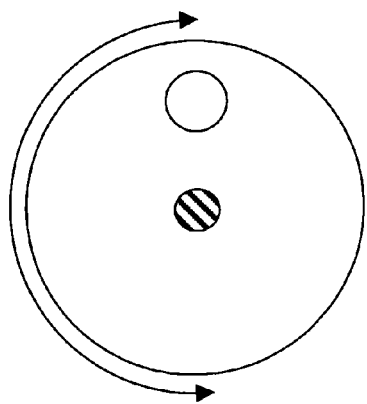
FIG. 10a shows a top view of a single-hole selector electrode.
Figure 10C:
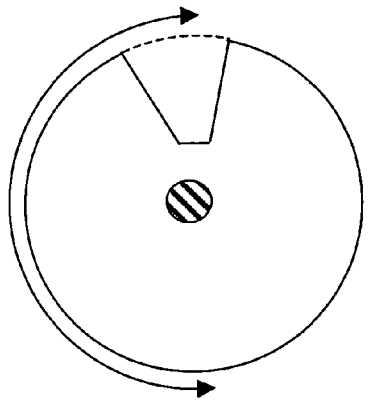
FIG. 10c shows a top view of a notched selector electrode.

Referring now to FIGS. 10a to 10d, shown are several examples of optional selector electrode configurations suitable for use with the various embodiments of the instant invention. FIG. 10a shows a top view of a single-hole selector electrode similar to the one described with reference to FIGS. 1 through 8b. FIG. 10b shows a double-hole selector electrode, in which rotation by 90° about a centrally mounted drive shaft is sufficient for switching between two ion inlet orifices into FAIMS. FIG. 10c shows a notched selector electrode, in which a portion of the selector electrode is cut away or the electrode is formed absent at least a portion of a sector. The shape of the notch in FIG. 10c is for illustrative purposes only, and other suitable shapes may be envisaged. Finally, FIG. 10d shows an alternative arrangement in which a drive shaft is eccentrically mounted to the ion selector electrode. Only a relatively small amount of rotation, relative to other embodiments, about the drive shaft is required to switch between two ion inlet orifices into FAIMS. Preferably, a not-illustrated barrier is provided between the openings in the selector electrode so as to prevent possible cross-talk between the sources and the openings.

Figure 11:
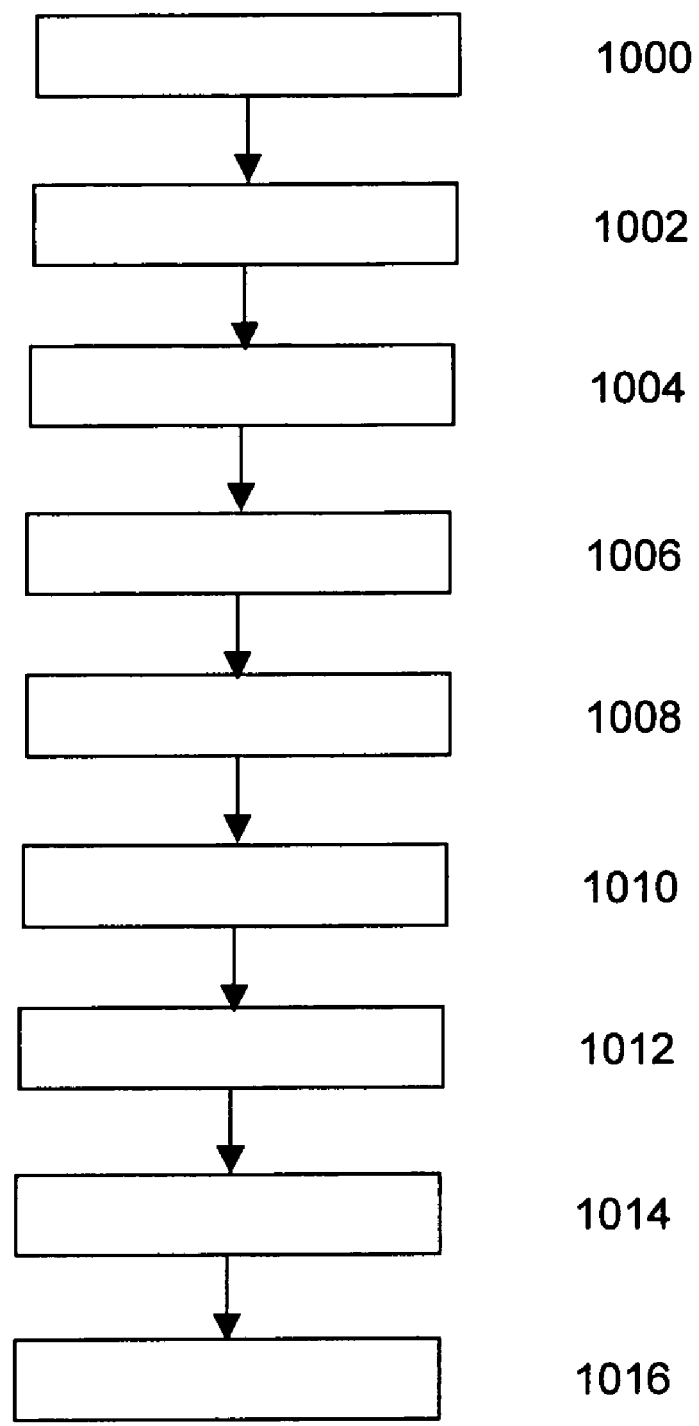
FIG. 11 is a simplified flow diagram of a method of separating ions according to an embodiment of the instant invention.

Referring now to FIG. 11, shown is a simplified flow diagram of a method for separating ions according to an embodiment of the instant invention. At step 1000, a FAIMS analyzer region is provided in fluid communication with an ion detector. At step 1002, a first ionization source is provided in communication with a sample material including a precursor of an ion type of interest. At step 1004, a second ionization source is provided in communication with a sample material including the precursor of the ion type of interest. Using the first ionization source, a mixture of ions is produced at step 1006, the mixture of ions comprising different types of ions including the ion type of interest. During a first period of time, the ions are directed at step 1008 from the first ionization source along a path of a first length through the FAIMS analyzer region, the first length being sufficient to effect at least a partial separation of the ion type of interest from other types of ions that may be in the mixture. Using the ion detector, ions are detected at step 1010 after the ions have traveled the first length. Using the second ionization source, a mixture of ions is produced at step 1012 comprising different types of ions including the ion type of interest. During a second period of time not overlapping with the first period of time, the ions are directed at step 1014 from the second ionization source along a path of a second length through the FAIMS analyzer region, the second length being insufficient to effect a separation of the ion type of interest from most other types of ions in the mixture. At step 1016 and using the ion detector, the ions are detected after the ions have traveled the second length.

Figure 12:
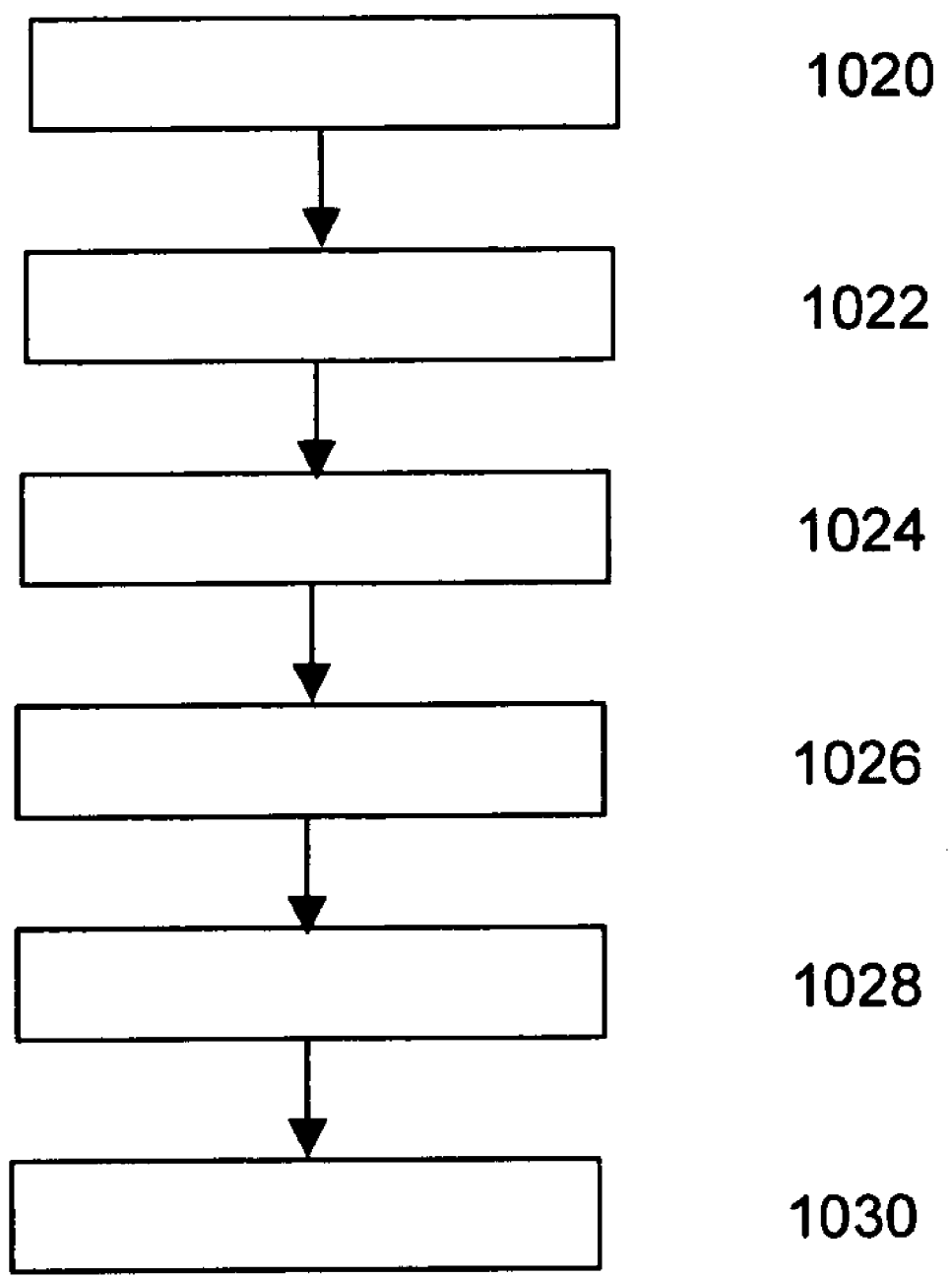
FIG. 12 is a simplified flow diagram of another method of separating ions according to an embodiment of the instant invention.

Referring now to FIG. 12, shown is a simplified flow diagram of another method for separating ions according to an embodiment of the instant invention. At step 1020 a FAIMS analyzer region is provided in fluid communication with an ion detector. At step 1022 a mixture of different types of ions including an ion type of interest is introduced into the analyzer region via a first ion inlet orifice. At step 1024 the ion type of interest is selectively transmitted through the analyzer region and to the ion detector. At step 1026 ions of a calibration compound are introduced into the analyzer region via a second ion inlet orifice. At step 1028 the ions of a calibration compound are transmitted to the ion detector. In dependence upon a response of the ion detector to the ions of a calibration compound, the ion detector initiates corrective action, if needed, at step 1030. Upon completion of this corrective action, the mixture of different types of ions including an ion type of interest is introduced into the analyzer region via a first ion inlet orifice, and this ion of interest is selectively transmitted through the analyzer region and to the ion detector. The measurements of the ion of interest taken after the corrective action are improved relative to those that would have been taken absent the corrective action.

Numerous other embodiments may be envisaged without departing from the spirit and scope of the invention.

What is claimed is:

1. An apparatus for separating ions, comprising:
a first electrode;
a second electrode disposed in a spaced-apart relationship with the first electrode, a space between the first electrode and the second electrode defining a FAIMS analyzer region therebetween, the FAIMS analyzer region in fluid communication with an ion outlet orifice;
a first ion inlet orifice defined within a first portion of the first electrode, the first ion inlet orifice spaced-apart from the ion outlet orifice by a first distance, such that ions introduced via the first ion inlet orifice travel the first distance through the FAIMS analyzer region between the first ion inlet orifice and the ion outlet orifice;
a second ion inlet orifice defined within a second portion of the first electrode, the second ion inlet orifice spaced-apart from the ion outlet orifice by a second distance that is shorter than the first distance, such that ions introduced via the second ion inlet orifice travel the second distance between the second ion inlet orifice and the ion outlet orifice; and,
an ion inlet orifice selector comprising a selector electrode having an opening defined therethrough, the selector electrode moveable between a first position in which the opening is aligned with the first ion inlet orifice for supporting introduction of a flow of ions into the FAIMS analyzer region via the first ion inlet orifice and a second position in which the opening is aligned with the second ion inlet orifice for supporting introduction of a flow of ions via the second ion inlet orifice.

2. An apparatus according to claim 1, comprising a power supply for applying an asymmetric waveform voltage and a direct current compensation voltage between the first electrode and the second electrode, to establish an electric field within the analyzer region for effecting a FAIMS-based separation of ions.

3. An apparatus according to claim 1, wherein the second distance is selected to provide an average ion flow path through the analyzer region that is sufficiently short to support simultaneous transmission of plural types of ions contained in a mixture of ions introduced via the second ion inlet orifice.

4. An apparatus according to claim 3, wherein the first distance is selected to provide an average ion flow path through the analyzer region that is sufficiently long to support at least partial separation of a first type of ion contained in a mixture of ions introduced via the first ion inlet orifice from a second type of ion contained in the same mixture.

5. An apparatus according to claim 1, wherein the ion inlet orifice selector comprises a motor rotationally coupled to the ion inlet selector, the motor for actuating the selector electrode between the first position and the second position.

6. An apparatus according to claim 5, wherein the ion inlet orifice selector comprises a drive shaft disposed between the motor and the selector electrode, the drive shaft for transferring rotational motion of the motor to the selector electrode.

7. An apparatus according to claim 1, comprising a first ionization source disposed adjacent to the first ion inlet orifice for providing a flow of analyte ions produced from a sample material for introduction via the first ion inlet orifice.

8. An apparatus according to claim 7, comprising a second ionization source disposed adjacent to the second ion inlet orifice for providing a flow of ions produced from a calibration compound for introduction via the second ion inlet orifice.

9. An apparatus according to claim 1, comprising a curtain plate electrode disposed between the selector electrode and the first electrode, the curtain plate electrode comprising a first curtain gas orifice for being aligned with the first ion inlet orifice when in an assembled condition, and comprising a second curtain gas orifice for being aligned with the second ion inlet orifice when in an assembled condition.

10. An apparatus according to claim 1, comprising an electrically insulating member mounted to the selector electrode and extending toward the first electrode a distance sufficient to form a substantially gas-tight seal between the electrically insulating member and one of the first portion of the first electrode and the second portion of the first electrode.

11. An apparatus according to claim 10, wherein the electrically insulating member is dimensioned for forming a substantially gas tight seal with the first electrode about either one of the first ion inlet orifice and the second ion inlet orifice, but not during a same overlapping period of time.

12. An apparatus according to claim 11, wherein the electrically insulating member is mounted to the selector electrode such that when one of the first ion inlet orifice and the second ion inlet orifice is aligned with the electrically insulating member, the other one of the first ion inlet orifice and the second ion inlet orifice is aligned with the opening through the selector electrode.

13. An apparatus according to claim 12 wherein the selector electrode is electrically insulated from the first electrode and forms a substantially gas-tight seal with the first electrode about the first and second portions thereof, so as to define a curtain gas region proximate the first ion inlet orifice and the second ion inlet orifice.

14. A method for separating ions, comprising:
providing a FAIMS analyzer region in fluid communication with an ion detector;
providing a first ionization source in communication with a sample material including a precursor of an ion type of interest;
providing a second ionization source in communication with a sample material including the precursor of the ion type of interest;
using the first ionization source, producing a mixture of ions comprising different types of ions including the ion type of interest;
during a first period of time, directing the ions from the first ionization source along a path of a first length through the FAIMS analyzer region, the first length being sufficient to effect at least a partial separation of the ion type of interest from other types of ions in the mixture;
using the ion detector, detecting ions after the ions have traveled the first length;
using the second ionization source, producing a mixture of ions comprising different types of ions including the ion type of interest;
during a second period of time not overlapping with the first period of time, directing the ions from the second ionization source along a path of a second length through the FAIMS analyzer region, the second length being insufficient to effect a separation of the ion type of interest from other types of ions in the mixture to a same extent as occurs along the path of the first length;
using the ion detector, detecting ions after the ions have traveled the second length.

15. A method according to claim 14, wherein more of the different types of ions are detected by the detector after the ions have traveled the path of a second length relative to a number of the different types of ions that are detected by the detector after the ions have traveled the path of a first length.

16. A method according to claim 14, wherein directing the ions from the first ionization source along a path of a first length through the FAIMS analyzer region comprises aligning an opening defined within a selector electrode with a first ion inlet into the FAIMS analyzer region.

17. A method according to claim 16, wherein directing the ions from the second ionization source along a path of a second length through the FAIMS analyzer region comprises aligning the opening defined within the selector electrode with a second ion inlet into the FAIMS analyzer region.

18. A method according to claim 17, wherein each one of the first ionization source and the second ionization source produce ions during the first period of time and the second period of time.

19. A method according to claim 18, comprising during a third period of time, moving the selector electrode from a first condition in which the opening is aligned with the first ion inlet into the FAIMS analyzer region to a second condition in which the opening is aligned with the second ion inlet into the FAIMS analyzer region.

20. A method according to claim 19, wherein the third period of time is short relative to both the first period of time and the second period of time.

21. A method according to claim 19, wherein moving the selector electrode comprises rotating the selector electrode.

22. A method according to claim 19, wherein the ion detector comprises a mass spectrometer, and wherein the mixture of ions produced by the second ionization source includes ions of a compound for calibrating the mass spectrometer.

23. A method for separating ions, comprising:
providing a FAIMS analyzer region in fluid communication with an ion detector;
introducing a mixture of different types of ions including an ion type of interest into the analyzer region via a first ion inlet orifice;
selectively transmitting the ion type of interest along a first distance through the FAIMS analyzer region from the first ion inlet to the ion detector;

introducing ions of a calibration compound into the FAIMS analyzer region via a second ion inlet orifice, the second ion inlet orifice positioned for use in calibration;

transmitting the ions of a calibration compound along a second distance shorter than the first distance through the FAIMS analyzer region from the second ion inlet to the ion detector; and, in dependence upon a response of the ion detector to the ions of a calibration compound, modifying at least one operational parameter of the ion detector.

24. A method according to claim 23, comprising providing a first ionization source in communication with a sample material including a precursor of the ion type of interest.

25. A method according to claim 24, wherein introducing a mixture of different types of ions comprises using the first ionization source to produce the mixture of ions comprising different types of ions including the ion type of interest and, during a first period of time, aligning an opening of a selector electrode between the first ionization source and a first ion inlet into the FAIMS analyzer region and selectively transmitting the ion type of interest through the analyzer region.

26. A method according to claim 25, comprising providing a second ionization source in communication with a material including a precursor of the ions of the calibration compound.

27. A method according to claim 26, wherein introducing ions of a calibration compound comprises using the second ionization source to produce the ions of the calibration compound and, during a second period of time not overlapping with the first period of time, aligning the opening of the selector electrode between the second ionization source and a second ion inlet into the FAIMS analyzer region and selectively transmitting the ions of the calibration compound through the analyzer region.

28. A method according to claim 27, comprising determining a measured mass-to-charge ratio of the ions of a calibration compound and in dependence upon a difference between the determined mass-to-charge ratio of the ions of a calibration compound and a known mass-to-charge ratio of the ions of a calibration compound, producing a revised mass-scale.

29. A method according to claim 28, comprising detecting the ion type of interest using the mass spectrometer and determining a mass-to-charge ratio of the ion type of interest based on the revised mass-scale.

30. A method for separating ions, comprising:

providing a FAIMS analyzer region in fluid communication with a mass spectrometric ion detector;

providing a first ionization source in communication with a sample material including a precursor of an ion type of interest;

providing a second ionization source in communication with a material including a precursor of a calibration compound ion;

using the first ionization source, producing a mixture of ions comprising different types of ions including the ion type of interest;

using the second ionization source, producing calibration compound ions from the precursor of the calibration compound ion;

during a first period of time, aligning an opening of a selector electrode between the second ionization source and a first ion inlet into the FAIMS analyzer region;

during the first period of time, directing the calibration compound ions from the second ionization source into the FAIMS analyzer region and transmitting the calibration compound ions along a first distance through the FAIMS analyzer region from the first ion inlet to the mass spectrometric ion detector;

detecting the calibration compound ions and determining the mass-to-charge ratio of the calibration compound ions;

calibrating the mass-scale in dependence upon a difference between the determined mass-to-charge ratio of the calibration compound ions and an expected mass-to-charge ratio of the calibration compound ions;

during a second period of tune not overlapping with the first period of time, aligning the opening of the selector electrode between the first ionization source and a second ion inlet into the FAIMS analyzer region;

during the second period of time, directing the ions from the first ionization source into the FAIMS analyzer region and selectively transmitting the ion type of interest along a second distance longer than the first distance through the FAIMS analyzer region from the second ion inlet to the mass spectrometric ion detector; and, detecting the ion type of interest using the mass spectrometric ion detector and determining the mass-to-charge ratio of the ion type of interest.

* * * * *

UNITED STATES PATENT AND TRADEMARK OFFICE
CERTIFICATE OF CORRECTION

PATENT NO.       : 7,223,971 B2                                                Page 1 of 1
APPLICATION NO.  : 11/068767
DATED            : May 29, 2007
INVENTOR(S)      : Guevremont et al.

It is certified that error appears in the above-identified patent and that said Letters Patent is hereby corrected as shown below:

Column 18, claim 30, line 32
The word "tune" should be replaced with --time--

Signed and Sealed this

Twenty-seventh Day of November, 2007

JON W. DUDAS
*Director of the United States Patent and Trademark Office*